(12) United States Patent
Cassidy et al.

(10) Patent No.: US 6,175,688 B1
(45) Date of Patent: Jan. 16, 2001

(54) WEARABLE INTRAVENOUS FLUID HEATER

(75) Inventors: David Cassidy, Chelmsford; Russell Hart, North Attleboro, both of MA (US)

(73) Assignee: Belmont Instrument Corporation, Billerica, MA (US)

( * ) Notice: Under 35 U.S.C. 154(b), the term of this patent shall be extended for 0 days.

(21) Appl. No.: 09/113,255

(22) Filed: Jul. 10, 1998

(51) Int. Cl.[7] .................................. A61F 7/00; F24H 1/08
(52) U.S. Cl. ......................... 392/470; 392/478; 604/113
(58) Field of Search .................................. 604/113, 114, 604/93; 392/465, 470, 467, 472, 474, 475, 478

(56) References Cited

U.S. PATENT DOCUMENTS

| | | |
|---|---|---|
| 3,399,536 | 9/1968 | Walz . |
| 3,443,060 | 5/1969 | Smith . |
| 3,475,590 | 10/1969 | Pins . |
| 3,485,245 | 12/1969 | Lahr et al. . |
| 3,590,215 | 6/1971 | Anderson . |
| 3,614,385 | 10/1971 | Horstmann . |
| 3,640,283 | 2/1972 | Bhatia et al. . |
| 3,853,479 | 12/1974 | Talonn et al. . |
| 4,038,519 | 7/1977 | Foucras . |
| 4,108,146 | 8/1978 | Golden . |
| 4,167,663 | 9/1979 | Granzow, Jr. et al. . |
| 4,293,762 | 10/1981 | Ogawa . |
| 4,309,592 | 1/1982 | Le Boeuf . |
| 4,314,143 | 2/1982 | Bilstad et al. . |
| 4,356,383 | 10/1982 | Dahlberg et al. . |
| 4,384,578 | 5/1983 | Winkler ............................... 604/114 |
| 4,464,563 | 8/1984 | Jewett . |
| 4,532,414 | 7/1985 | Shah et al. . |
| 4,574,876 | 3/1986 | Aid . |
| 4,678,460 | 7/1987 | Rosner . |
| 4,680,445 | 7/1987 | Ogawa . |
| 4,707,587 | 11/1987 | Greenblatt . |
| 4,731,072 | 3/1988 | Aid . |
| 4,759,749 | 7/1988 | Verkaart . |
| 4,782,212 | 11/1988 | Bakke . |
| 4,801,777 | 1/1989 | Auerbach . |
| 4,844,074 | 7/1989 | Kurucz . |
| 4,847,470 | 7/1989 | Bakke . |
| 4,878,537 | 11/1989 | Verkaart . |

(List continued on next page.)

FOREIGN PATENT DOCUMENTS

| | | |
|---|---|---|
| 9318886 U | 3/1994 | (DE) . |
| WO92/17040 | 10/1992 | (WO) . |

OTHER PUBLICATIONS

PCT Notification of Transmittal of the International Search Report of Serial No. PCT/US99/13627, Nov. 8, 1999.
International Search Report of Serial No. PCT/US99/13627, Nov. 8, 1999.
PCT Invitation To Restrict Or To Pay Additional Fees for International Application No. PCT/uss99/13627, International Filing Date 16/06/99.

*Primary Examiner*—Teresa Walberg
*Assistant Examiner*—Thor Campbell
(74) *Attorney, Agent, or Firm*—Cesari and McKenna

(57) ABSTRACT

An intravenous fluid heater is provided that is dimensioned so as to be wearable adjacent a patient's intravenous fluid infusion situs. In one embodiment, the heater includes a heat exchanger for defining a flow path through the heater for fluid to be infused via the infusion situs. At least one controllable heating element is provided for heating the fluid in the flow path by heat conduction thereto through the heat exchanger. Sensors are included for sensing respective temperatures of entering and exiting fluids of the flow path. A controller controls, based upon the temperatures of the exiting fluids, heating of the fluid in the flow path by the heating element so as to cause the fluid in the flow path to be substantially uniformly heated to a desired infusion temperature prior to exiting the heater.

51 Claims, 17 Drawing Sheets

U.S. PATENT DOCUMENTS

| | | |
|---|---|---|
| 4,906,816 | 3/1990 | van Leerdam . |
| 4,908,014 | 3/1990 | Kroyer . |
| 4,938,279 | 7/1990 | Betker . |
| 4,962,761 | 10/1990 | Golden . |
| 5,062,775 * | 11/1991 | Orth .................................. 417/477.3 |
| 5,108,372 | 4/1992 | Swenson ............................. 604/113 |
| 5,125,069 | 6/1992 | O'Boyle . |
| 5,188,604 * | 2/1993 | Orth ..................................... 604/153 |
| 5,245,693 | 9/1993 | Ford et al. . |
| 5,250,032 | 10/1993 | Carter, Jr. et al. ................... 604/113 |
| 5,254,094 | 10/1993 | Starkey et al. . |
| 5,344,568 * | 9/1994 | Kitaevich et al. ................... 210/645 |
| 5,381,510 | 1/1995 | Ford et al. . |
| 5,690,815 * | 11/1997 | Krasnoff et al. . |
| 5,702,358 * | 12/1997 | Witherspoon et al. ................... 604/4 |
| 5,846,224 * | 12/1998 | Sword et al. ........................ 604/113 |

* cited by examiner

WEARABLE INTRAVENOUS FLUID HEATER

BACKGROUND OF THE INVENTION

1. Field of the Invention

The present invention relates generally to a device for heating to a desired infusion temperature a fluid to be supplied intravenously to a patient. More specifically, it relates to such a device that is (1) dimensioned to be wearable on the patient adjacent to the infusion situs (i.e., the location on the patient's body were the fluid is to be infused into the patient), and (2) configured to determine automatically when, and to provide warning if, the fluid flow rate in the device falls below a desired minimum threshold therefor, and/or gas (e.g., air) is present in the fluid. Although the present invention finds particular utility in heating of fluids which are to be supplied intravenously at relatively low flow rates (e.g., below about 2550 ml/hour for fluids to be heated to an infusion temperature of between 38–42 degrees C. from an input temperature into the device of 10 degrees C., or below about 3600 ml/hour for fluids to be heated to such an infusion temperature from an input temperature of 18 degrees C.), it should be understood that other utilities are also contemplated for the present invention (e.g., infusion of intravenous fluids at other temperatures and flow rates).

2. Brief Description of Related Prior Art

Many prior art techniques and devices exist for warming fluids to be infused intravenously into humans and other animals. One such conventional device is disclosed in U.S. Pat. No. 5,245,693 ("the '693 patent"). The '693 patent is directed to an intravenous fluid heater that includes a disposable cassette containing a heat exchanger. The preferred embodiment of the heat exchanger disclosed in the '693 patent includes a passageway-defining inner layer sandwiched between a pair of flexible, metal foil membranes. The inner layer defines an extended, e.g., serpentine, path for fluid to be warmed, and serves to space apart and insulate the metal foil membranes from one another. Inlet and outlet ports to the serpentine fluid path are defined in one of the two foil membranes. Heat generated by heating elements which sandwich the heat exchanger is transferred through the metal foil membranes to the fluid flowing through the serpentine path. The heating elements are designed to be graduated, that is, to generate more heat in the area of the inlet portion of the serpentine path than in the area of its outlet.

Unfortunately, the heating device disclosed in the '693 patent suffers from several disadvantages. First, since the heating elements of the '693 device apply non-uniform, graduated heating to the fluid traversing the flow path, the risk exists that, depending upon the fluid flow rate through the flow path, the fluid may become overheated (i.e., heated above the desired target temperature for infusion) at the portion of the heating elements applying elevated amounts of heat to the fluid. If sufficiently elevated, such overheating can damage certain types of intravenously delivered fluids (e.g., blood and blood-products, if the overheating is above about 41 degrees C.).

Also, the heating device disclosed in the '693 patent is not wearable by the patient adjacent the fluid infusion situs. This means that the length of tubing required to deliver the heated fluid from the device to the infusion situs may vary depending upon where the device is positioned relative to the patient, but will always be longer than that which would be required if the device were being worn by the patient at or near the infusion situs. This means that in the infusion arrangement disclosed in the '693 patent, the temperature of the heated fluid exiting the heating device will always drop, prior to being infused into the patient, more than would be the case if the heating device were wearable adjacent the infusion situs. The temperature drop of the heated fluid can be especially pronounced at the aforesaid relatively low fluid flow rates. Unfortunately, a significant proportion of intravenous fluid infusions take place at such low flow rates.

A yet further disadvantage of the '693 patent's heating arrangement is that although means are included for reducing gas bubble formation in the infusion fluid, no means are provided for automatically determining whether such bubbles are present in the fluid or whether there has been reduction in fluid flow rate, and for taking appropriate action (e.g., providing warning and/or stopping fluid flow into the patient) in the event such conditions are determined to be present. As will be appreciated by those skilled in the art, if left unchecked these types of conditions can be, at minimum, deleterious to patient well-being, and at most, life-threatening.

An additional disadvantage of the heating device disclosed in the '639 patent results from its use of metal foil membranes. As was acknowledged by the patentee of the '639 patent during prosecution of said patent, if such metal foil membranes become distorted in use, the fluid being heated can become "spot heated" to elevated temperatures at the locations of such distortions. Such spot heating can result in damage to the fluid being heated.

Another conventional infusion fluid warming device is disclosed in U.S. Pat. No. 5,254,094 ("the '094 patent"). In the arrangement disclosed in the '094 patent, a box which may be attached to a patient's arm is provided. Two chambers are included in the box, containing a heat exchanger element constructed from a continuous length of stainless steel tubing in the form of two parallel coils which are connected to each other by a straight length of tubing. The box includes a passage between the chambers such that a warming fluid may be introduced through an aperture in the box into one of the chambers, flow into the other chamber, and then exit the warmer through another aperture in the box. The infusion fluid to be warmed is supplied to the coils through a first flexible plastic inlet tube and discharged for infusion into a patient through a second flexible plastic tube. The warming fluid is supplied via fluid supply tubing to the box from a separate fluid source that is not dimensioned or suitable for being worn by the patient, such as a water heater. A temperature sensor located in the infusion fluid path between the box and the infusion situs may be provided for generating signals indicative of the temperature of the infusion fluid for provision to a microprocessor contained in the same unit comprising the water heater. The microprocessor also receives outputs from a water temperature sensor and controls the water heater, based upon the outputs from these sensors and a desired infusion fluid temperature set by the user, so as to maintain the heating water at a temperature for heating the infusion fluid to the desired temperature.

Disadvantageously, use of a warming fluid/infusion fluid type of heat exchanger, and a warming fluid heater that is remote from the heat exchanger and not wearable by the patient, make '094 patent's arrangement bulky, and relatively difficult to move and set up for use. Also disadvantageously, if even a single crack, pin-hole, imperfect seal, or other opening exists in the infusion fluid tubing/fittings in the heat exchanger, the infusion fluid may become contaminated with the warming fluid. Additionally, as is the case in the '693 patent, the '094 patent discloses no means for automatically determining whether gas bubbles are present in the infusion fluid or there has been reduction in infusion fluid flow rate, and for taking appropriate action (e.g., providing warning and/or stopping fluid flow into the patient) in event such conditions are determined to be present.

Other examples of infusion fluid warming prior art are disclosed in U.S. Pat. Nos. 5,381,510, 4,731,072, 3,443,060, 3,475,590, 3,485,245, 3,590,215, 3,614,385, 3,640,283, 3,853,479, 4,038,519, 4,108,146, 4,167,663, 4,293,762, 4,309,592, 4,938,279, 4,847,470, 4,574,876, 3,399,536, 4,962,761, 5,125,069, 4,908,014, 4,906,816, 4,844,074, 4,707,587, 4,759,749, 4,782,212, 4,801,777, 4,680,445, 4,678,460, 4,532,414, 4,464,563, 4,314,143, 4,356,383, and 4,878,537. Unfortunately, the prior art disclosed in each of these patents suffers from the aforesaid and/or other disadvantages and drawbacks.

SUMMARY OF THE INVENTION

In accordance with the present invention, an intravenous fluid heater is provided that is dimensioned to be wearable adjacent a patient's intravenous fluid infusion situs. In one embodiment of the present invention, the heater includes a heat exchanger for defining a flow path through the heater for fluid to be infused via the infusion situs. At least one controllable heating element is provided for heating the fluid in the flow path by heat conduction thereto through the heat exchanger. Sensors are included in the heater for sensing respective temperatures of entering and exiting fluids of the flow path. A controller controls, based upon at least one of the entering and exiting fluid temperatures, heating of the fluid in the flow path by the heating element. The fluid in the flow path is substantially uniformly heated to a desired infusion temperature prior to exiting the heater.

The controller may be programmed to determine, based at least in part upon one or both of the entering/exiting fluid temperatures, whether the flow rate of fluid is below a desired threshold value therefor, and/or whether gas is present in the flow path. The controller may also be programmed to initiate provision of a warning/indication to a user of the device, and/or to initiate other appropriate action (e.g., closing a valve in the device to prevent further flow of fluid to the patient), when one or both of the aforesaid conditions are present.

The at least one heating element may include two heating elements, and the heat exchanger may include two flexible walls for contacting a member inserted between the flexible sheets for defining together with the flexible sheets the flow path. The flexible walls are preferably made of plastic. Advantageously, use of these plastic walls permit this embodiment of the present invention to overcome the aforesaid disadvantages that result from use of the metal foil membranes in the '693 patent's heating device.

The device of this embodiment of the present invention may also include an electrically insulating external housing and disposable cover for enclosing the aforesaid components of the device so as to prevent contamination of same and risk of electric shock injury to the patient wearing the device. The heat exchanger may be unattached to the remainder of the device and may be held in place in the device by forces applied to the exchanger by the mechanism used to lock the housing in place about the other components of the device. Advantageously, this permits both the cover and heat exchanger to be disposable/replaceable, and the remainder of the device to be reusable.

The heating element may include at least one metal plate for contacting the heat exchanger and an electrical resistance heater, controlled by the controller, for controllably heating the plate. The electrical resistance heater may include a printed circuit board etched metal layer. A thermally conductive, electrically insulating layer may be positioned between the etched metal layer and plate. The controller, sensors, and metal layer may all be part of a single, double-sided circuit board.

Thus, in accordance with the present invention, the entire intravenous fluid heater (i.e., the heat exchanger, heating element(s), sensors, controller, etc.) may be comprised within a single protective enclosure and dimensioned so as to be wearable adjacent the patient's infusion situs. The controller may be programmed to detect presence of reduced fluid flow and/or air in the fluid flow, and to warn and/or prevent further supply of the fluid upon detection of conditions. Additionally, the heating elements are completely solid, and no warming fluid is used to heat the infusion fluid. Advantageously, the above features provided in accordance with the present invention permit the present invention to overcome the aforesaid and other disadvantages of the '693 and '094 patents.

Other features and advantages of the present invention will become apparent as the following Detailed Description proceeds and upon reference to the Drawings, wherein like numerals depict like parts, and in which:

BRIEF DESCRIPTION OF THE DRAWINGS

The description below refers to the accompanying drawings.

Figure 1:
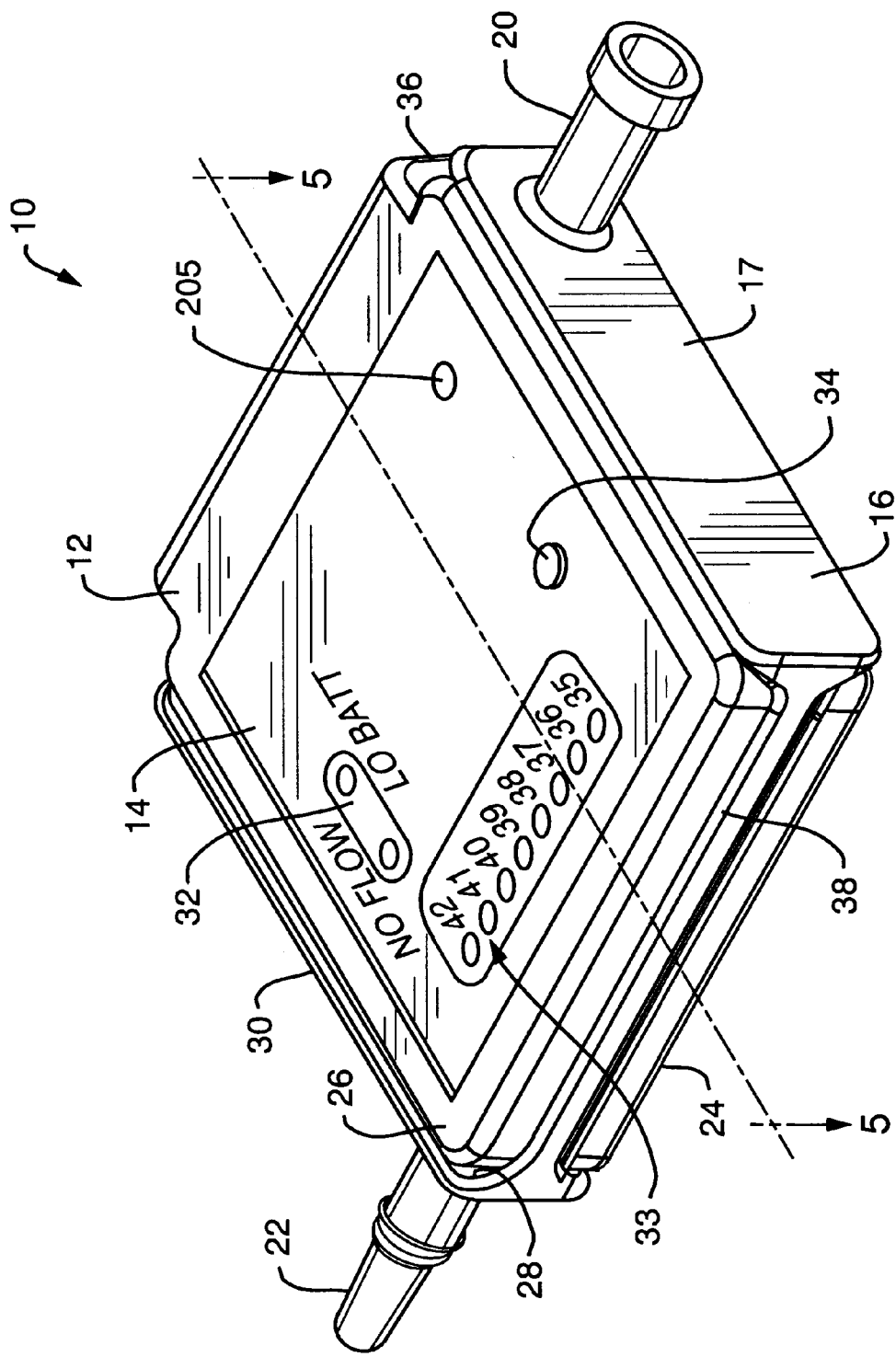
FIG. 1 is an outside perspective view of one embodiment of the intravenous fluid heater of present invention, wherein the strap mechanism for fastening the heater to the patient has been removed for purposes of clarity of illustration.
Figure 2:
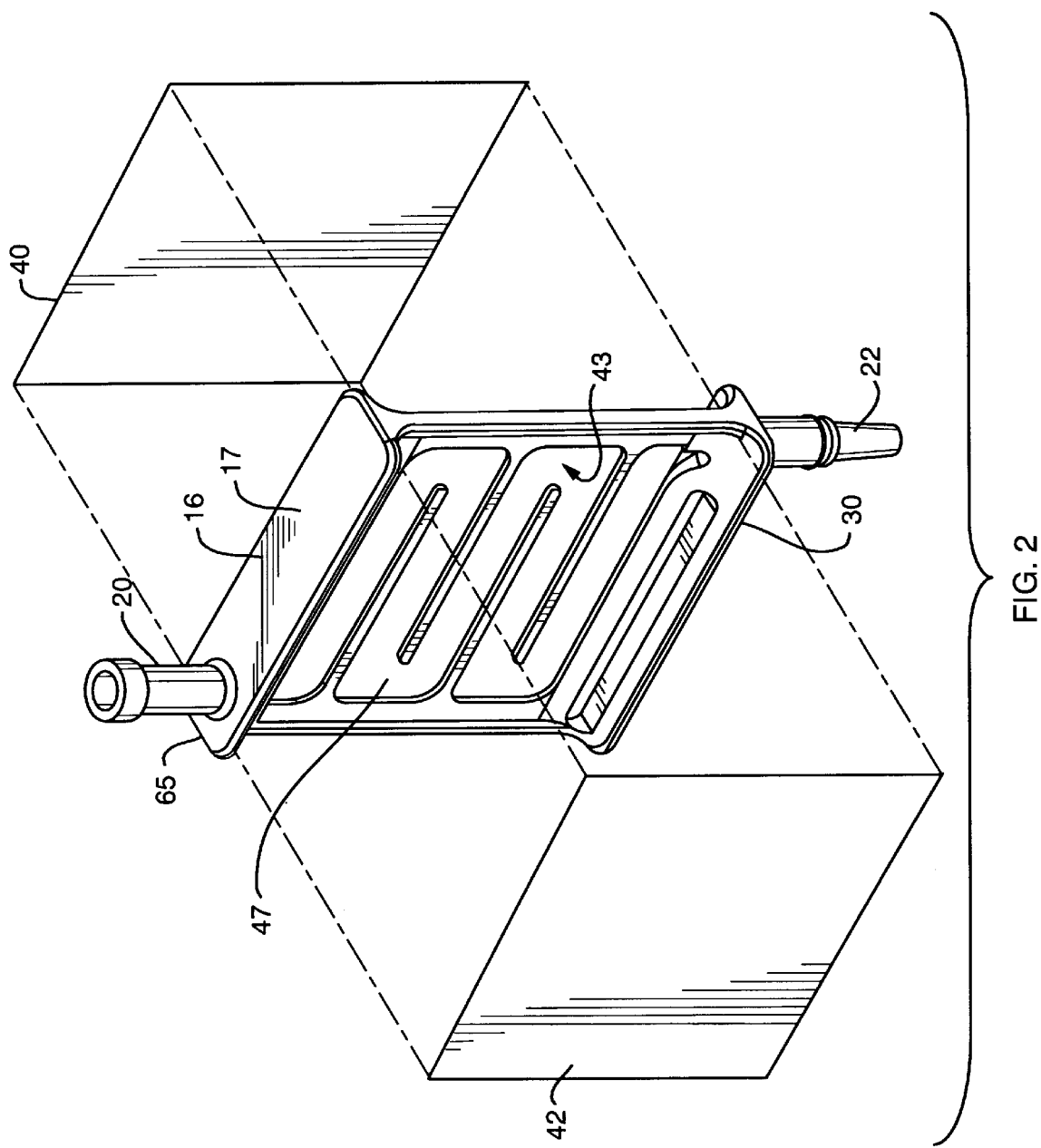
FIG. 2 is an exploded perspective view of the disposable heat exchanger of the embodiment of FIG. 1.
Figure 3:
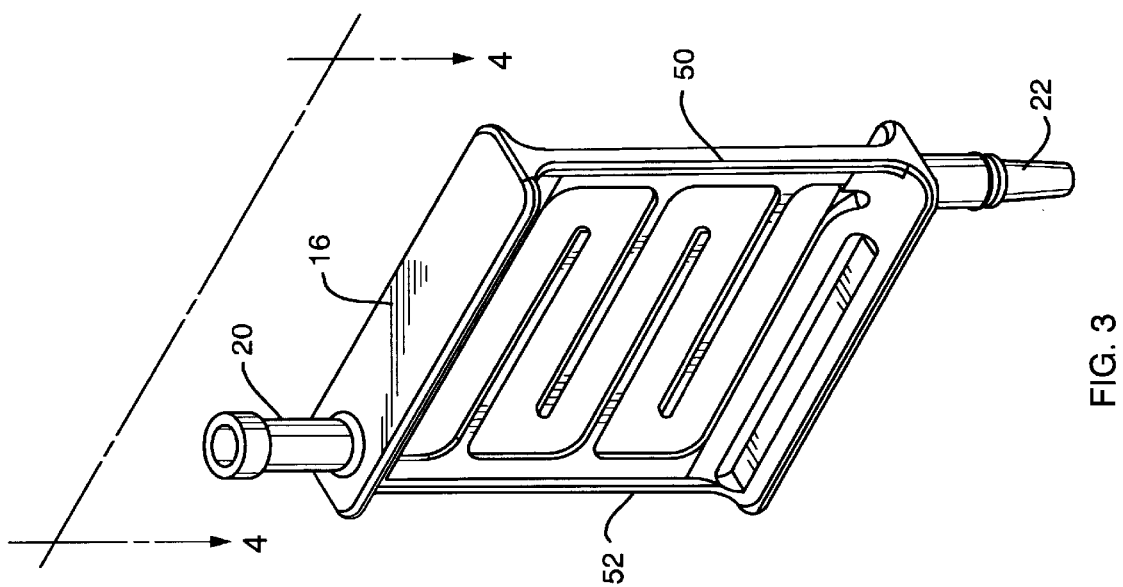
FIG. 3 is a perspective view of the portion of the disposable heat exchanger of FIG. 2 that defines a serpentine flow path for the infusion fluid.
Figure 4:
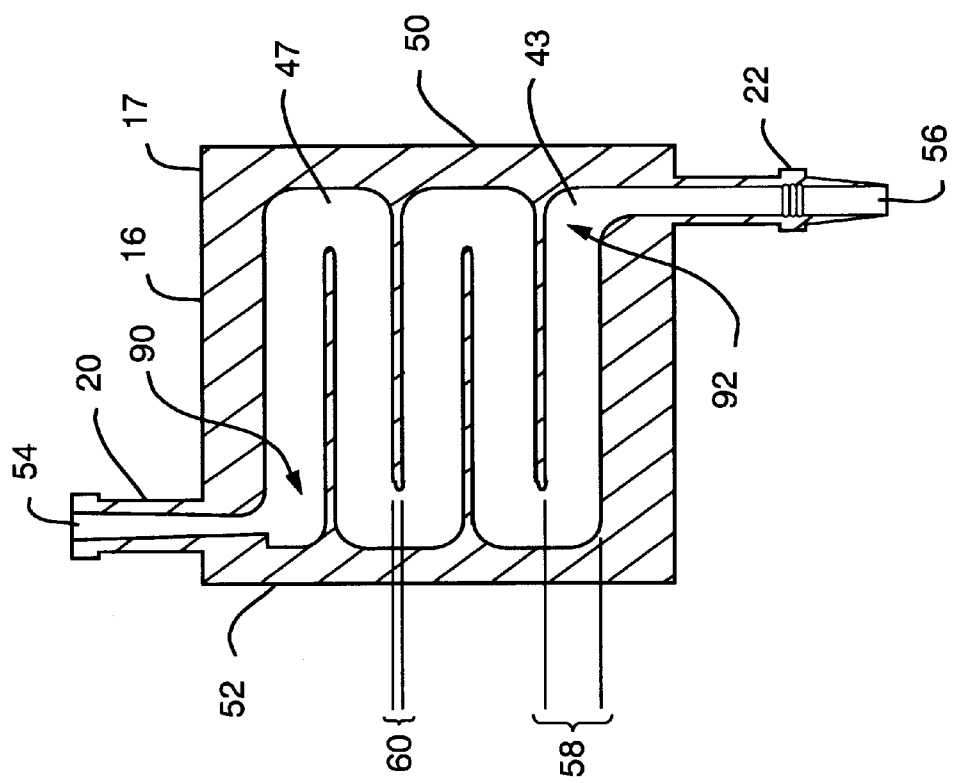
FIG. 4 is a cross-sectional view taken along lines 4—4 of FIG. 3.
Figure 5:
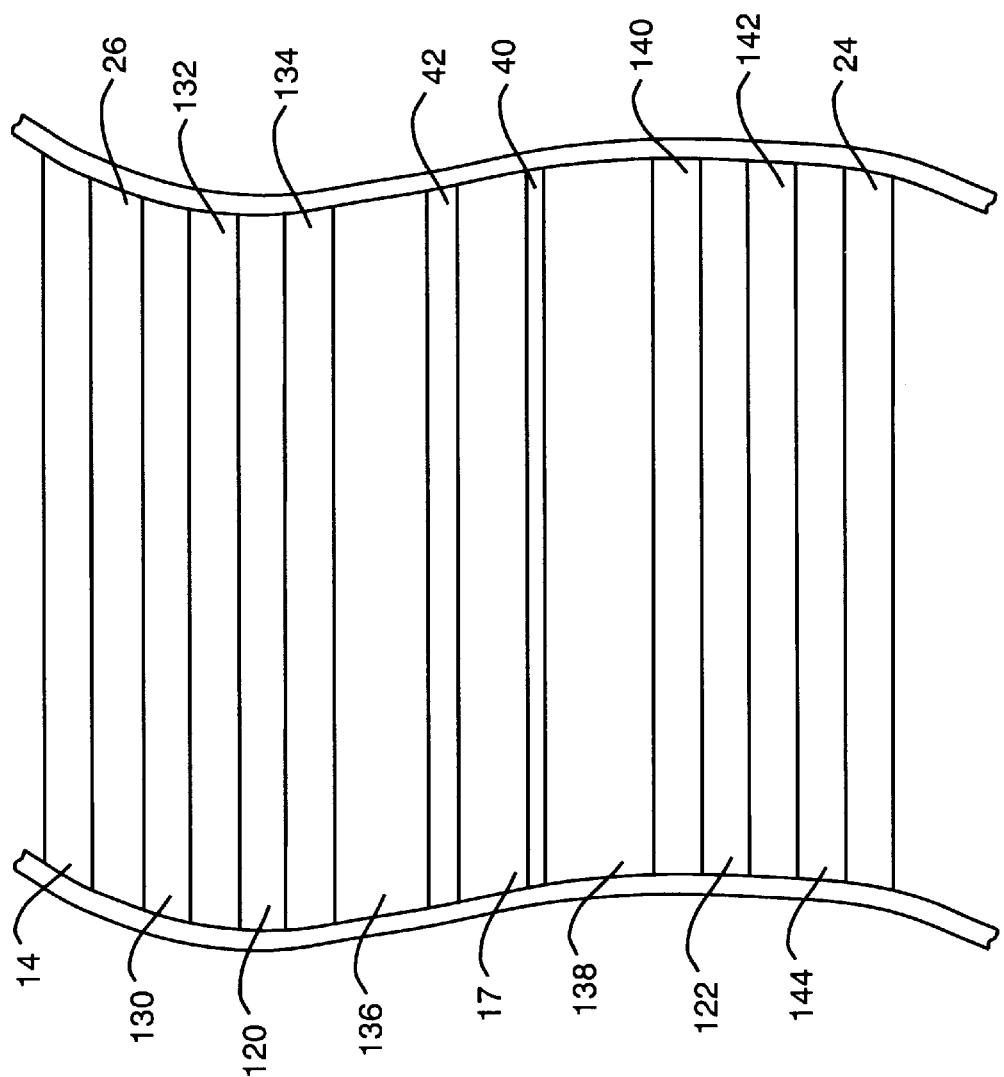
FIG. 5 is a highly schematic, partial cross-sectional view taken along lines 5—5 of FIG. 1 for illustrating, in a general fashion, the layered construction of the embodiment of FIG. 1.
Figure 6:
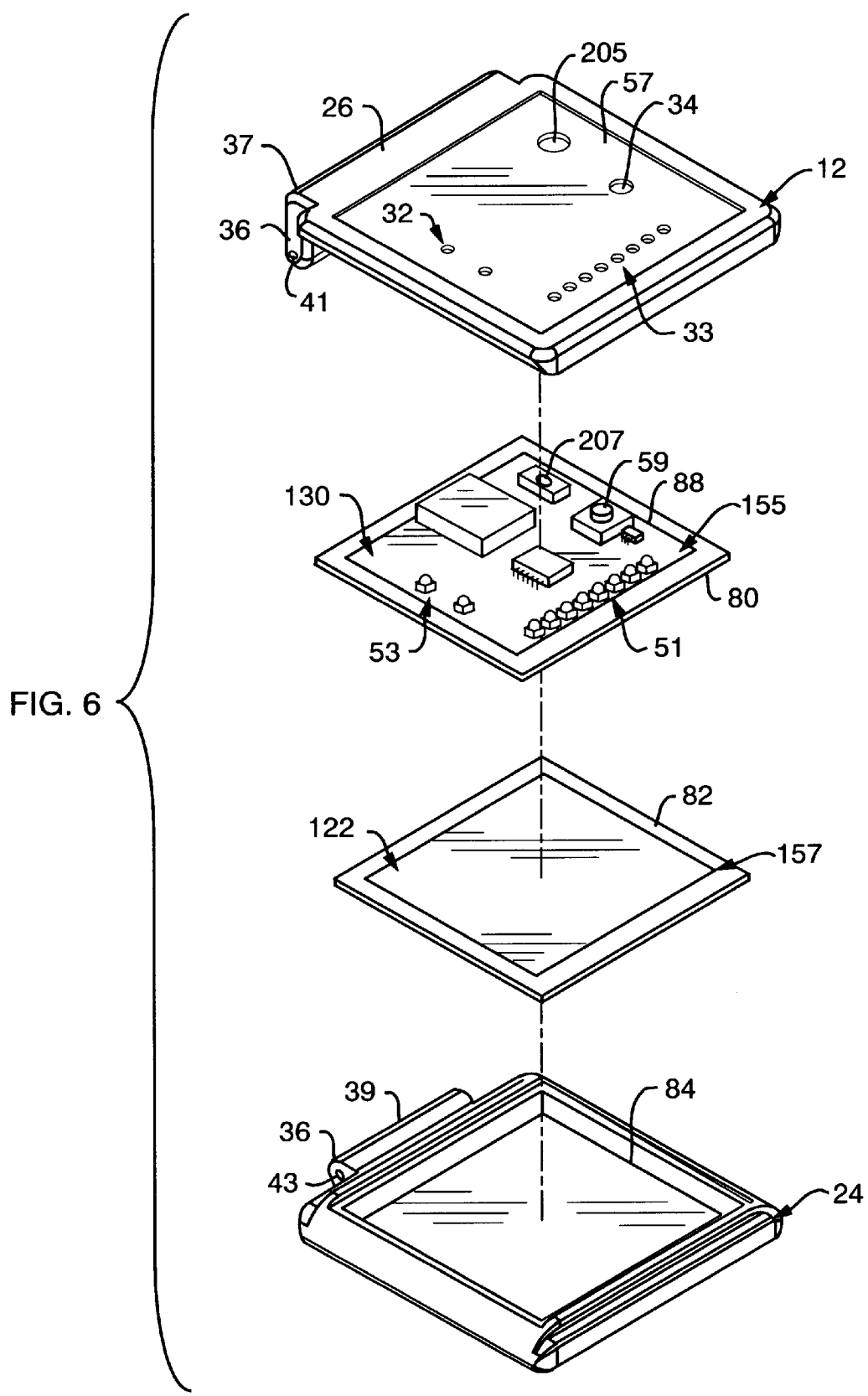
FIG. 6 is an exploded, schematic view illustrating the construction of the embodiment of FIG. 1, with the heat exchanger of FIG. 2 and the top indicator plate removed.

Although the following Detailed Description will proceed with reference being made to preferred embodiments thereof and methods of use, it will be appreciated by those skilled in the art that the present invention is not intended to be limited to these preferred embodiments and methods of use. Rather, the present invention is intended to be viewed quite broadly as being limited only as set forth in the hereinafter appended claims.

DETAILED DESCRIPTION OF ILLUSTRATIVE EMBODIMENTS

FIGS. 1–12A and 12B and 15 depict one preferred embodiment 10 of the wearable infusion fluid heater of the present invention. Heater 10 comprises a hard plastic housing 12 in the form of two generally square-shaped members 24, 26 joined via a locking hinge mechanism 36. Hinge mechanism 36 comprises an upper hinge portion 37 and mating lower hinge portion 39. These hinge portions 37, 39 are pivotably connected to each other via conventional means (e.g., a bolt, screw, or similar means, not shown) fastened into the common opening through the portions 37, 39 formed when the portions 37, 39 are mated with each other and the respective openings 41,43 of the portions 37, 39 are in coaxial alignment with each other. Openings 41,43 extend longitudinally through the hinge portions 37, 39.

A rectangular indicator face plate 14 is slightly undersized relative to rectangular recessed area 57 of top plate 26 and is attached there at via conventional means (e.g., glue or other type of bonding material) to the top plate 26. Indicator plate 14 includes a plurality of openings (collectively referred to by numerals 32,33) to permit viewing of light emitting diode (LED) indicators 51,53, and opening 34 for permitting user access to and activation of alarm mute button 59, attached to the top side 88 of circuit board 155. Similarly, plate 14 may include an opening 205 for permitting user access to and activation of heater on/off power button 207 attached to the top side 88 of circuit board 155. Alternatively, plate 14 may be replaced by a relatively thin, flexible membrane, having appropriate transparent portions (e.g., for viewing indicators 51, 53) and through which the buttons 59, 207 may be activated and deactivated.

Plate 14 also includes written/numerical descriptions of the information conveyed by activation of LED indicators 51, 53, and the functions that are toggled by buttons 59 and 207. More specifically, indicators 51 indicate the output temperature of the infusion fluid from the heater 10 in one degree increments from 35 degrees C. to 42 degrees C. Activation of the "No Flow" LED of indicators 53 indicates that the flow rate of infusion fluid through the heater 10 is below a predetermined minimum desired therefor, while activation of the "Lo Batt" indicator LED indicates that the power level being supplied from the power supply 116 has fallen to a degree sufficient to inhibit proper operation of the heater 10. Likewise, although not shown in the Figures, a separate indicator LED may be provided on board 155, and displayed through the plate 14 for indicating if air is present in the flow path 43 through the heater 10.

When the heater 10 is in use (i.e., heating fluid to be infused to the patient), the housing 12 almost completely encloses a heat exchanger 17. The heat exchanger 17 comprises a member 65 of unitary construction, and two flexible sheets 40, 42. Member 65 preferably is made of plastic (e.g., polyester), and is formed by injection molding. Infusion fluid flow path 43 through the heater 10 is defined by the flexible sheets 40, 42 together with the member 65, and includes fluid inlet 20, fluid outlet 22, and serpentine channel 47 between inlet 20 and outlet 22. Inlet 20 comprises a female lure fitting for being mated to a corresponding male lure fitting (not shown) whereby to permit the heat exchanger 17 to receive via tubing 600 connected to the corresponding fitting, an unheated flow of infusion fluid from an external infusion fluid source (not shown); inlet 22 comprises a male lure fitting for being mated to a corresponding female lure fitting 602 whereby to permit transmission, via tubing 604 connected to the corresponding female fitting, of the heated infusion fluid from the heater 10 to infusion situs 606 of the patient 608. A releasable strap mechanism (e.g., a hook and loop or adhesive tape fastening system) 610 permits the heater 10 to be worn by the patient adjacent the situs 606.

The square flexible sheets 40, 42 are identically dimensioned, contact respective internal sides of flared portions 16, 30, 50, 52 of the member 65, and completely cover from opposite respective sides of the member 65 the channel 47. Each of the flexible walls 40, 42 preferably is a highly flexible, polyester plastic film, sputter-coated with an outer bond-coating of acrylic, and is physically bonded (e.g., via ultrasonic welding) by this acrylic layer to the bond-coating of the acrylic outer layer on the member 65, but is not physically attached to any other part of the heater 10.

In use, the heat exchanger 17 is sandwiched between circuit boards 155, 157 such that the bottom and top surfaces 80, 82 of the boards 155, 157, respectively are in intimate contact with the flexible walls 42, 40, respectively. Board 157 is undersized with respect to a square recess 84 formed in plates 24 into which panel 157 fits. It should be understood that although not shown in the Figures, a similar recess is formed in the top plate 26 for receiving the top panel 155.

Panels 155, 157 preferably each comprise Thermal Clad Bond Ply® base layers (commercially available from The Berquist Company of Minneapolis, Minn.), to which are bonded respective the electronic components 100. More specifically, panel 155 may include a double-sided circuit board comprising two copper etch layers 120, 130 disposed upon and separated by a fiberglass substrate 132. Various of the electronic components of heater 10 are surface mounted or otherwise formed on and connected to etch layer 130. Etch layer 120 is connected to the etch layer 130 via appropriate conventional means (e.g., connection through holes, etc.) and comprises a resistive heating element. The resistive heating element 120 is physically separated from an aluminum or copper plate heat sink 136 by an electrically insulating, but highly thermally conductive layer 134. Layer 134 may comprise a ceramic-filled, glass-reinforced polymer material. When heater 10 is in use, layer 136 is in intimate contact with flexible wall 42. Layers 120, 130, 132, 134, and 136 are all laminated together to form a solid, single circuit panel 155.

Circuit board 157 comprises a respective double-sided circuit board made up of copper etch layers 122, 144 separated by a fiberglass substrate 142. Etch layer 142 is electrically connected to etch layer 130 via a connection wire (not shown), and various of the electronics 100 of the heater 10 are surface mounted or otherwise formed on and connected to etch layer 142. Etch layer 122 is connected to the copper etch layer 144 via appropriate conventional means (e.g., connection through holes, etc.) and comprises another resistive heating element. The resistive heating element 122 is physically separated from an aluminum or copper plate heat sink 138 by an electrically insulating, but highly thermally conductive layer 140 of the same construction as layer 134. When heater 10 is in use, layer 138 is in intimate contact with flexible wall 40. A connection wire (not shown) electrically connects the traces 130, 144. Layers 122, 138, 140, 142, and 144 are all laminated together to form a solid single circuit board 157.

Hinge mechanism 36 permits the plates 24, 26 to be rotated relative to each other from the closed position shown in FIG. 1, to an open position (not shown). The hinge mechanism 36 also includes a conventional releasable locking mechanism for locking the plates 24, 26 into the closed position when they are moved from the open position into the closed position (i.e., when sufficient force is applied to plates 24,26 for moving the plates 24, 26 to the open position). In the closed position, the plates 24, 26 clamp onto and come into sealing engagement with the flanged portions of the heat exchanger and with top and bottom flexible walls 42, 40, respectively, so as to form an air and liquid tight seal that prevents communication to and from the internal portion of the heater 10 enclosed by the housing 12, except via the inlet and outlet of the heat exchanger 17. Also in the closed position, the lower surface 80 of panel 155 is urged and held in place by the housing 12 in contact with flexible wall 42 and the upper surface 82 of panel 157 is urged and held in contact with flexible wall 40. In the open position of the housing 12, the circuit board members 155, 157 and the heat exchanger 17 may be accessed and removed from the housing 12. It is important to note that the heat exchanger 17 is not physically bonded to the rest of the assembly 10. Thus, when the clamping forces provided to the heat exchanger 17 by the housing 12 when the housing 12 is in its closed, locked position, are removed (i.e., when the hinge mechanism 36 is unlocked, and the plates 24, 26 are in the open position), the heat exchanger 17 may be disposed of and replaced with a fresh (i.e., unused) replacement heat exchanger. Additionally, although not shown in the Figures, in use, the assembly 10 is covered with an outer plastic contamination-preventing cover which may also be removed, discarded, and replaced, after use of device 10 on a patient. Thus, the assembly 10 may be reused on another patient, without substantial risk of contamination or other biohazard to that subsequent patient.

Figure 7:
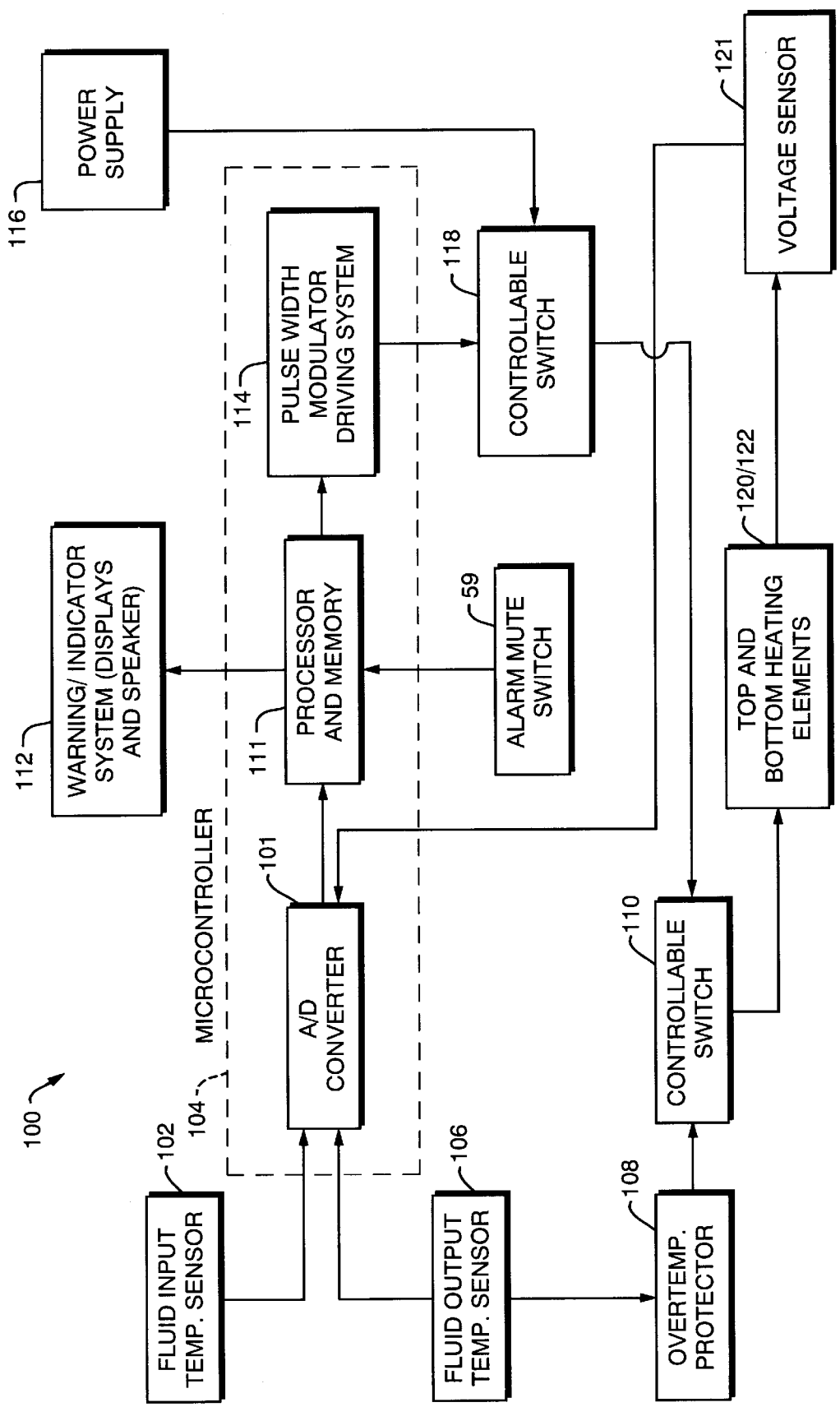
FIG. 7 is a highly schematic, functional block diagram of the electronics used in the embodiment of FIG. 1.
Figure 8:
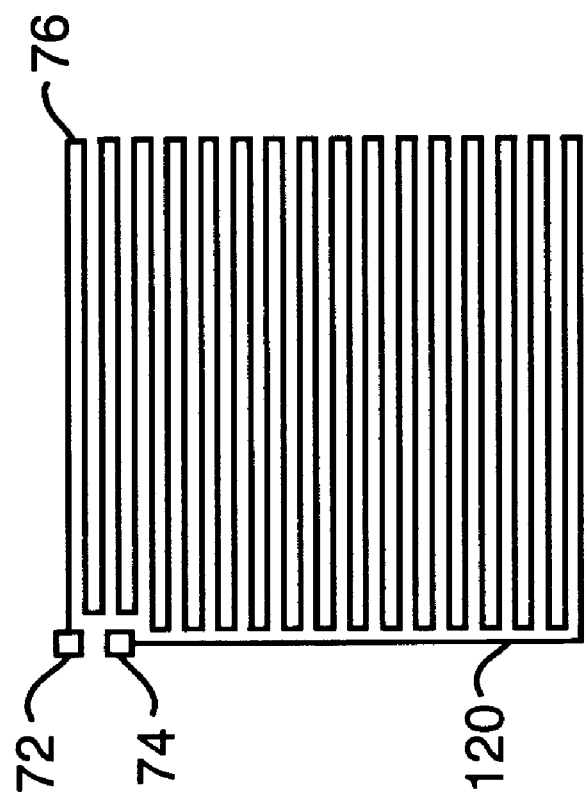
FIG. 8 illustrates the electrically conductive etchings used to heat the infusion fluid in the embodiment of FIG. 1.

FIG. 8 shows the copper trace pattern comprising heating element 120. It should be understood that although not shown in the Figures, heating element 122 (e.g., shown in schematic form in FIG. 6) comprises the same trace pattern. As shown in FIG. 8, element 120 comprises a plurality of copper trace turns 76, and two connector pads 72, 74, one of which is connected to the controllable switch 110 (FIG. 7), and the other being connected to ground potential. Energizing of the elements 120, 122 with electrical power from source 116 causes the heating elements 120, 122 to heat up, and this heat is supplied via heat conduction through the layers 134, 136, 138, and 140 to the heat exchanger 17, and thence into the fluid flowing through the flow path 43. The construction of layers 120, 122, 134, 136, 138, and 140 is such that substantially uniform heating is applied to the fluid flowing through flow path 43. Thus, elements 120, 134, and 136 may be said to constitute a single conductive heating element, and elements 122, 138, and 140 may be said to constitute another such heating element.

The electronic components 100 of the heater 10 comprise a single chip microcontroller 104. Microcontroller 104 preferably comprises a 16C715 chip available from Microchip Technology, Inc. of Chandler, Ariz., and has integrated circuits for implementing analog-to-digital converter 101, processor and associated ROM/RAM memory 111, and pulse width modulation power driver control system 114 functions. It should be appreciated that although not shown in FIG. 7, power supply 116 preferably comprises a plurality of power supplying circuits (i.e., for supplying different voltages and currents appropriate for powering the different types of circuits comprising the components 100 functionally represented in FIG. 7), and supplies power to microcontroller 104, temperature sensors 102, 106, over temperature protection circuit 108, and mute switch 59, based upon the current state of the power switch 207 (i.e., whether it is in an "on" state or an "off" state). Power supply 116 may comprise a battery power supply system, and/or may rectify alternating current (AC) received from an external source (not shown) via an external connection (also not shown) to generate direct current (DC) suitable for supply to the circuits comprising components 100. It should be appreciated that the power supply button 207 may be replaced by a power switch (not shown) that is part of the AC power connection.

Converter 101 receives analog voltage signals from infusion fluid input and output temperature sensors 102, 106. These sensors 102, 106 preferably comprise respective thermistors that are connected to copper etch pattern 130 and positioned directly above the inlet portion 90 and outlet portion 92, respectively, of channel 47. These signals from the sensors 102, 106 are digitized by the converter 101 and are supplied to the processor and memory 111, which then processes the digitized signals, in a manner that will be described more fully below, to determine the input and output temperatures of the infusion fluid (i.e., the temperature of infusion fluid at inlet 90 prior to being heated by the heater 10, and at outlet 92 after being heated by the heater 10, respectively).

Converter 101 also receives analog input signals from voltage sensor 121. These signals from the voltage sensor 121 indicate the instantaneous voltage across one or both of the heating elements 120, 122, are also digitized by the converter 101, and the digitized signals are supplied by the converter 101 to the processor 111. As will be described more fully below, processor 111 utilizes them together with the digitized signals from the sensors 102, 106 to generate control signals for controlling the warning/indicator system 112 and pulse width modulated signal generator 114. Of course, if the components 100 are appropriately modified, sensor 121 may be eliminated, and the voltage from one or both of the heating elements may be determined directly by supply of the digitized voltage(s) across the element(s) to the processor 111. System 112 includes the indicators 32, 33 and a speaker system (not shown) for sounding audible alarms. The pulse width modulated signals generated by system 114 control the state of switch 118, which switch 118 controls supply of power from supply 116 to the heating elements 120 and 122. Alarm mute switch 59 permits a user (not shown) to selectively disable the processor 111 from being able to command the system 112 to generate audible alarms.

Overtemperature protection circuit 108 deactivates heating elements 120, 122 when the output temperature of the infusion fluid exceeds a predetermined maximum temperature (e.g., 42 degrees C.), by controlling switch 110 to prevent power from being supplied to the elements 120 and 122; so long as the temperature at the outlet 92 of the channel 47 remains below this maximum threshold, the protector 108 maintains the switch 110 in a state that does not prevent the supply of power to the elements 120, 122. Each of switches 110, 118 may comprise transistor-based switching circuits.

Figure 9:
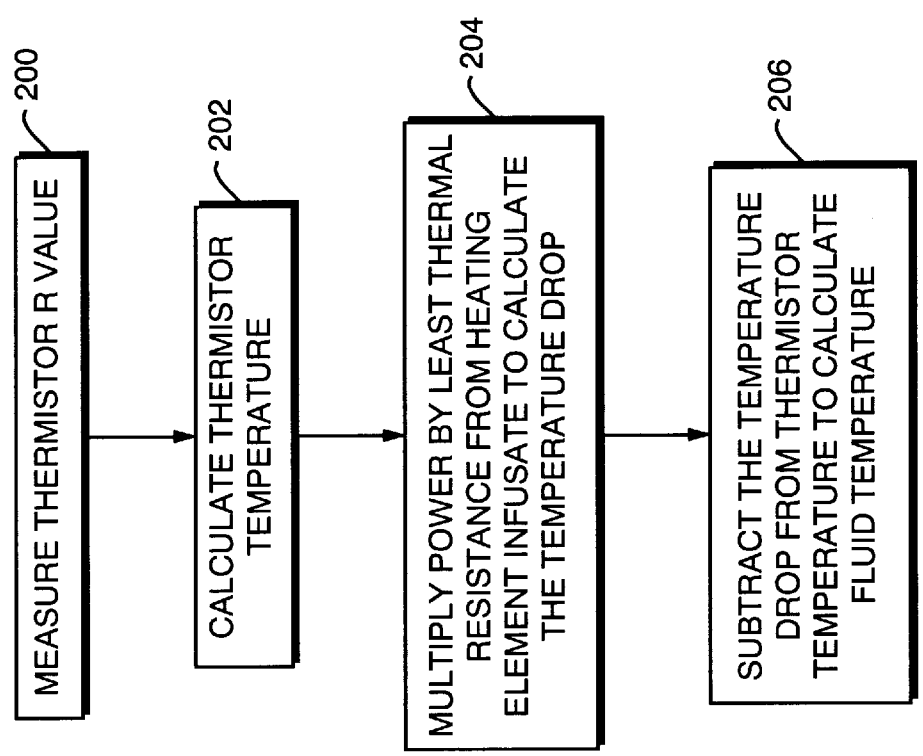
FIG. 9 is a flowchart of the fluid temperature measurement method used in the embodiment of FIG. 1.

Turning now to FIG. 9, one method used by processor 111 to determine the input fluid temperatures using the digitized signal from the sensor 102 will now be described. In the method, the digitized signals from the 102 are first used by the processor 111 to calculate the present resistance of the thermistor comprised in the sensor 102. (See, block 200). As is known to those skilled in the art, one of the properties of a thermistor is that its resistance changes in a predictable way with changes in its temperature. Thus, the circuit comprising the sensor 102 must be constructed in such a way as to permit the voltage signals supplied by the sensor 102 to be truly indicative of the present resistance of the thermistor comprised in the sensor 102. The relationship between the output voltage of the sensor 102 and the resistance of the thermistor comprised in the sensor 102 may be determined empirically, and the processor and memory 111 uses this relationship to determine the present resistance of thermistor based upon the output voltage of the sensor 102. Likewise, the relationship between the present resistance of the thermistor of sensor 102 and its temperature may be determined empirically, and the processor and memory 111 may use this relationship to calculate the present temperature of the thermistor, once the present resistance of the thermistor has been determined. (See, block 202)

However, during use of the heater 10, the present temperature of the thermistor of sensor 102 is higher than the present temperature at the inlet 90. This is due to the thermistor's relatively close proximity to the heating element 120 and the drop in temperature that occurs from the sensor 102 to the infusion fluid in the inlet 90 of the channel 47, due to the thermal resistance that exists in the layers 42, 134, and 136 (the thermal drop across layer 132 is substantially negligible). The processor 111 determines the actual temperature at the inlet 90 by calculating this temperature drop and subtracting the temperature drop from the calculated temperature of the thermistor of sensor 102.

More specifically, processor 111 calculates the temperature drop by calculating heating energy being output by the heating element 120 based upon the duty cycle of the pulse width modulated signals that the processor 111 commands the driving system 114 to generate, and then multiplies the heating energy by the thermal resistance from the heating element 120 to the inlet 90. The heating energy being output by the element 120 is calculated based upon the relationship between the total electrical power (derived from the pulse width modulated signals' duty cycle) delivered to the heating element 120 and the heating energy supplied from the heating elements 120 as a result of supply of said power, which relationship is empirically determined and preprogrammed into the processor 111. Likewise, the thermal resistance of the layers 42, 134, and 136 is determined empirically, and preprogrammed into the processor 111. It is assumed for purposes of these calculations that all of the heating energy supplied by the element 122 is absorbed by elements 40, 138, 140 and the fluid in the flow path. Device 10 is constructed so as to permit this to be an accurate assumption. Once the total temperature drop across layers 42, 134, and 136 is determined, the temperature drop is subtracted out from the temperature of the thermistor of sensor 102 to yield the temperature of the fluid at the inlet 90.

The same procedure as that discussed above for determining the temperature of the fluid at the inlet 90 is also used by the processor 111 to determine the temperature of the fluid at the outlet 92. Of course, it is the digitized voltage signal from sensor 106, rather than that from sensor 102, that is used by processor 111 to determine the output fluid temperature. Once the output fluid temperature is determined, processor 111 generates signals that activate an appropriate one of the LEDs of system 112 to indicate this temperature. Additionally, if the output fluid temperature exceeds a predetermined maximum therefor (e.g., 42 degrees C.), the processor 111 may cause the system 114 to immediately cease heating of the fluid by heating elements 120, 122, and cause a speaker comprised in the system 112 to generate an audible warning.

Figure 10:
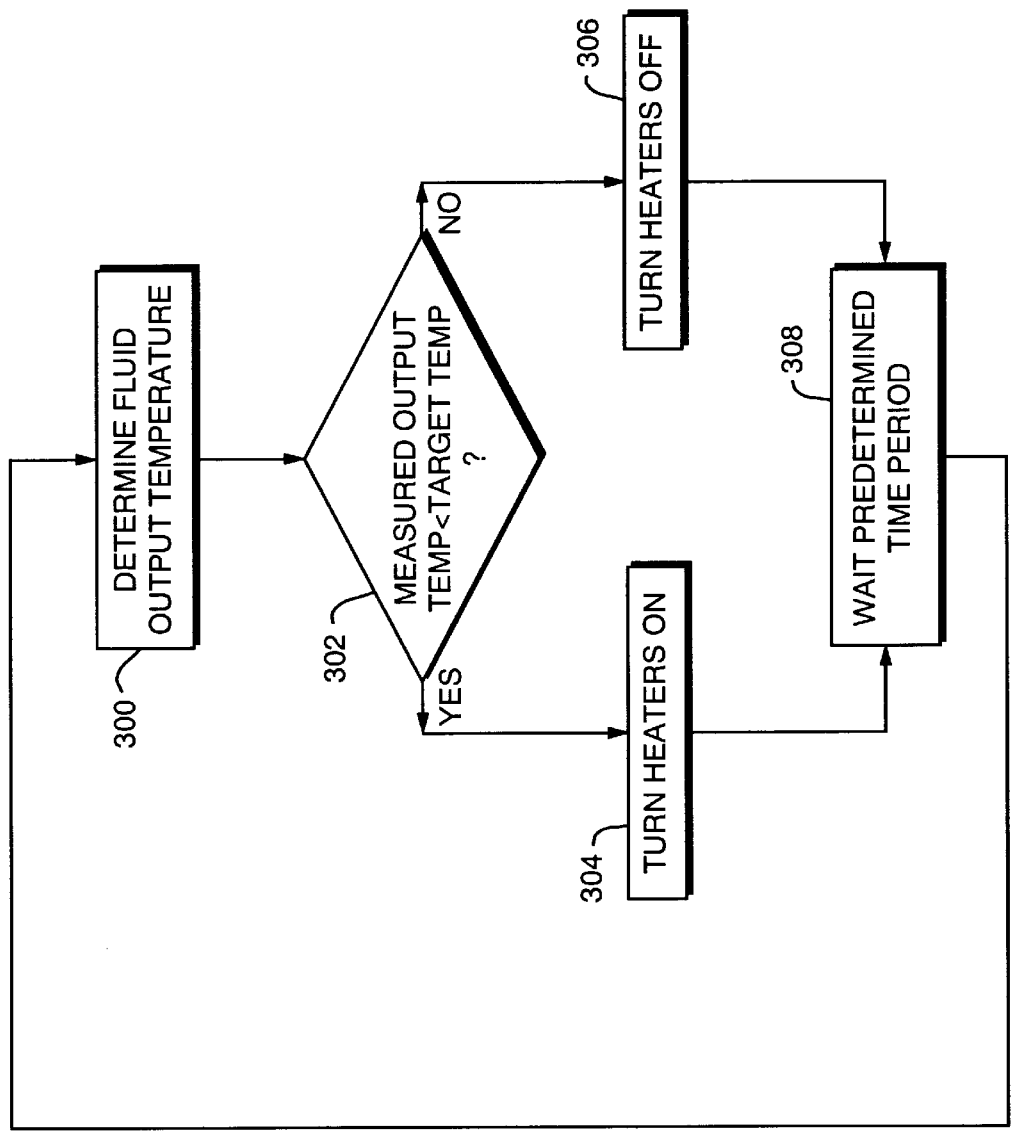
FIG. 10 is a flowchart of one fluid heating control method that can be used in the embodiment of FIG. 1.

FIG. 10 illustrates steps of one method that can be used by the processor 111 to control heating of the fluid by the heater 10. According to this method, once the output fluid temperature is determined using the afore described procedure (see block 300), the processor 111 determines whether the output fluid temperature is less than a predetermined target output fluid temperature (e.g., 40 degrees C.), and if the output temperature is less than this target temperature, the processor 111 causes the system 114 to initiate or maintain heating of the fluid in the flow path 43 by the heating elements 120, 122 (See, blocks 302 and 304). Alternatively, if the processor 111 determines that the output fluid temperature is greater than the target temperature (but less than the predetermined maximum temperature), the processor 111 may command the system 114 to cease heating of the fluid in the flow path 43 by the heating elements 120, 122. (See, block 306). Thereafter, the processor 111 may wait a predetermined time period (e.g., several milliseconds), and then begin the control process again at block 300.

Figure 11:
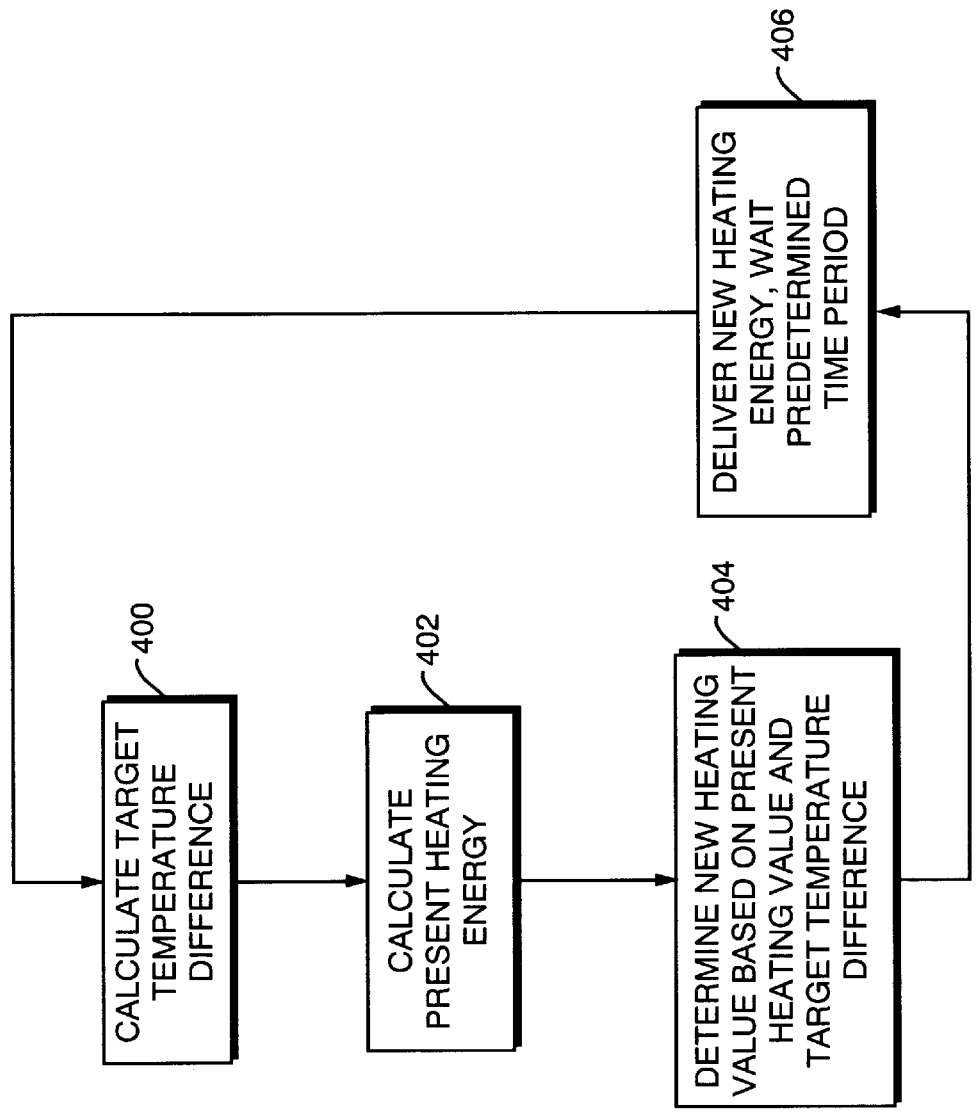
FIG. 11 is a flowchart of another fluid heating control method that can be used in the embodiment of FIG. 1.

Steps of an alternate method that may be used by the processor 111 to control the heating of the infusion fluid in the flow path 43 by the heating elements 120, 122 is shown in FIG. 11. Processor 111 begins this method by calculating the difference between the output fluid temperature determined in the manner described above, and a target temperature therefor (e.g., 40 degrees C.). (See, block 400) The processor 111 then calculates the heating energy being output by both the heating elements 120, 122, based upon the duty cycle of the pulse width modulated signals supplied by system 114 to switch 118. (See, block 402). The processor 111 then calculates the heating energy required to be output by the heating elements 120, 122 to raise the output temperature of the fluid to the target temperature, based upon an empirically determined relationship between the amount of heating energy supplied by the heating elements 120, 122 and expected temperature rise in the output temperature of the fluid, assuming a predetermined flow rate of the fluid through the flow path 43 (e.g., between about 2550 and 3600 ml/hour). (See, block 404) This relationship is preprogrammed into the processor and memory 111. Once the processor 111 determines this new heating energy, it controls the system 114 so as to cause same to output pulse width modulated signals having a duty cycle that causes the heating elements 120, 122 to output the new heating energy. (See block 406). The processor then waits a predetermined amount of time (e.g., several milliseconds), and begins the process again at block 400.

Figure 12A:
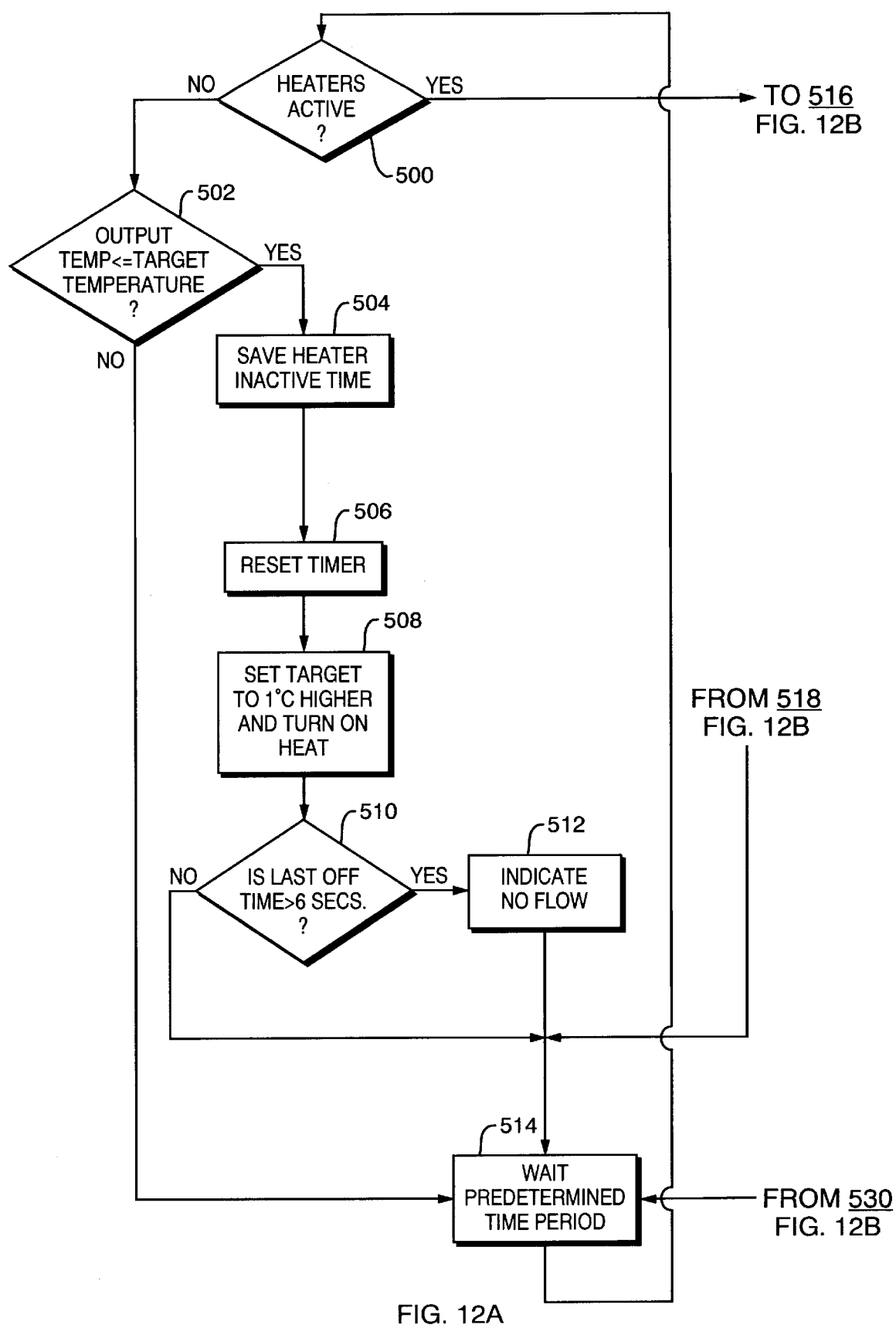
FIGS. 12A and 12B are flowcharts of a process used in the embodiment of FIG. 1 to determine whether gas is present in, and/or fluid flow rate through the heat exchanger's fluid flow path is below a desired minimum value therefor.
Figure 12B:
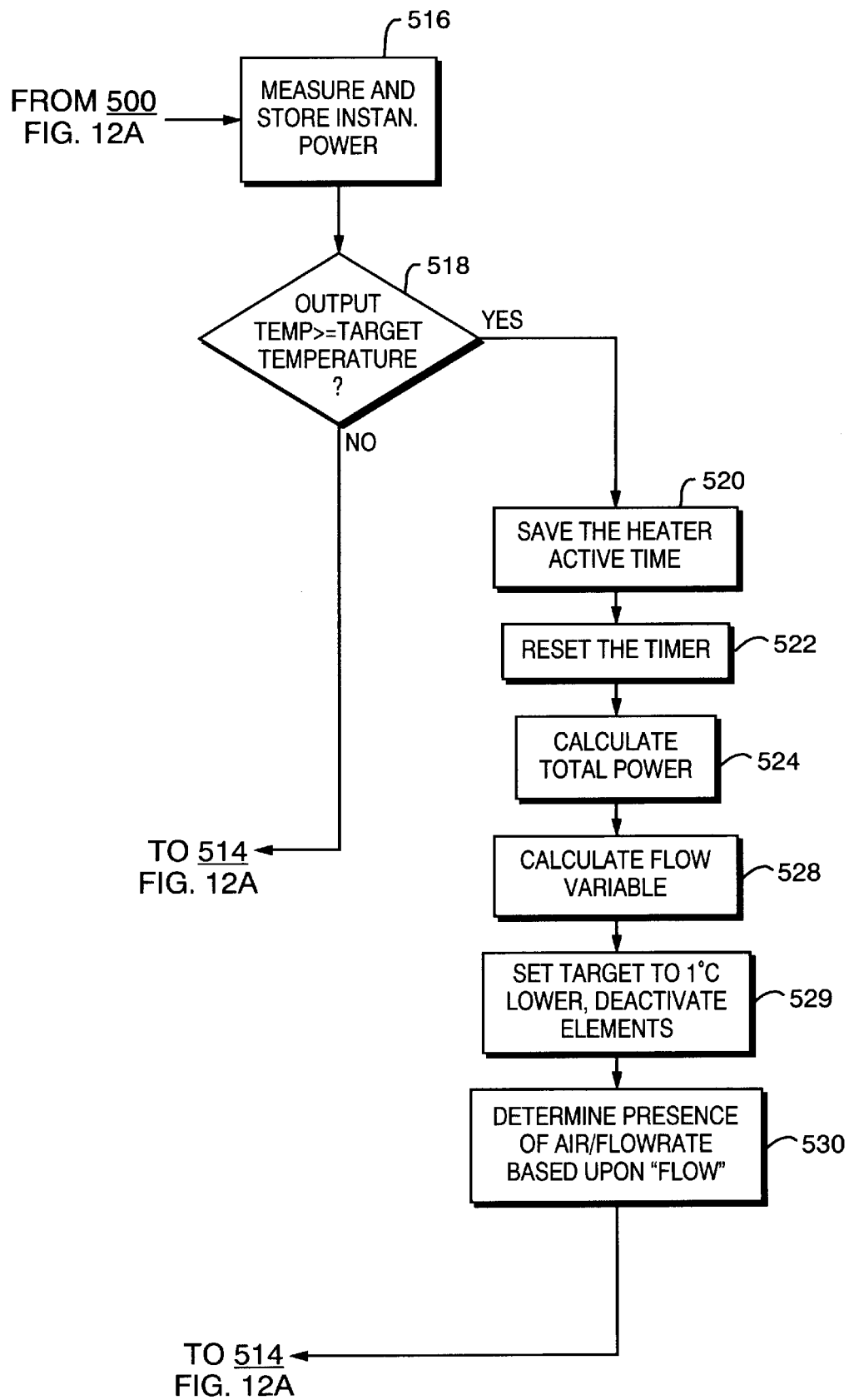

FIGS. 12A and 12B illustrate steps of one method used by the processor 111 to determine whether air is present in the flow path 43 and/or that the flow rate of fluid in the flow path 43 is below a desired minimum threshold value therefor. Processor 111 begins this method by determining whether the heating elements 120, 122 are in an active state (i.e., being energized by the power source 116), based upon the pulse width modulated signals being generated by the system 114. If the heating elements 120, 122 are in an active state, the instantaneous power being delivered to heating elements 120, 122 is calculated by the processor 111 based upon the electrical resistances of the heating elements 120, 122 and the instantaneous voltages across the heating elements sensed by the voltage sensor 121. The electrical resistances of the heating elements 120, 122 are preferably equal to each other, and are preprogrammed in the processor 111. The processor 111 then continues the process of FIGS. 12A and 12B by determining whether the output fluid temperature, determined as described above, is greater than or equal to a predetermined target temperature (e.g., 40 degrees). If the output fluid temperature is at least equal to the target temperature, the amount of time that the heaters 120, 122 have been most recently active is saved by the processor in memory (see block 520), and a timer used to determine the most recent active time of the heating elements 120, 122 is reset. (See, block 522) The total power delivered to the heating elements 120, 122 is then calculated based upon the previously stored instantaneous power and the length of time of the previous period of activation. Thereafter, a time constant (determined empirically and preprogrammed into the processor 111), equal to the time the heater 10 would take based upon the total power supplied to the heating elements 120, 122 during the most recent activation period to heat the infusion fluid from the input fluid temperature to the target temperature if the fluid in the flow path 43 is not flowing, is subtracted from the length of time of the most recent period of activation of the heating elements 120, 122. (See, block 524). The result of this subtraction is then used to determine whether air is present in the flow path 43 and/or the flow rate of the fluid through the flow path 43 is less than desirable. (See, block 530). Prior to making the determination at block 530, however, the processor 111 sets the target temperature to a value that is one degree C. lower than that to which it is presently set, and deactivates the heating elements 120, 122. (See, block 529)

At block 530, the processor 111 determines whether the value of the "flow" variable (i.e., the time constant subtracted from the length of the most recent period of activity of the heating elements 120, 122) is less than zero, and/or is at zero, or between zero and a minimum acceptable flow rate value. If the calculated flow variable is less than zero, the processor 111 determines that air is present in the flow path 43, since air can be heated more quickly that the fluid. If the calculated flow variable is at zero or between zero and the minimum flow rate value, the processor 111 determines that the flow rate through the flow path 43 is less than desirable. In either case, the processor 111 generates signals which cause appropriate LED indicator(s) of system 112 to be activated and/or audible warnings to be sounded.

After either carrying out the process steps of block 530 or determining at block 518 that the output fluid temperature is less than the target temperature, the processor 111 then waits a predetermined time period (block 514), and returns to carry out the step at block 500.

If at block 500, the processor 111 determines that the heating elements 120, 122 are not activated, the processor 111 proceeds to determine whether the output fluid temperature is less than or equal to the target temperature. If so, the processor 111 saves in memory the current amount of time that the heating elements 120, 122 have been deactivated and resets the timer used to determine this time. (See, blocks 502, 504, and 506). Thereafter, the processor 111 sets the target temperature to be one degree higher that the value to which it was previously set (block 508), and determines whether the current time of deactivation saved at block 504 is greater than an empirically determined amount of time (e.g., 6 seconds) within which the outlet 92 temperature should cool to the target temperature if sufficient fluid flow is present in the flow path 43. (See block 510) If the current time of deactivation is greater than this predetermined amount of time, the processor 111 determines that the flow rate in the path 43 is less than desirable, and signals this condition in the afore described manner. (See block 512)

After processing the steps at block 512, or if either the output fluid temperature is determined at block 502 to be greater than the target temperature or the current time of deactivation is determined at block 510 to be less the predetermined time period, the processor 111 undertakes the previously described action at block 514. After processing the action at block 514, the processor 111 loops back to begin the process of FIGS. 12A and 12B again at decision block 500.

Overtemperature protection circuit 108 generates control signals which control the state of switch 110 based upon the voltage signals supplied from the sensor 106. Circuit 108 may comprise an operational amplifier configured as a comparitor for comparing the voltage signals from the sensor 106 to a reference voltage signal indicative of a maximum desired output fluid temperature (e.g., 42 degrees C.). The protector circuit 108 generates signals based upon this comparison that cause the switch 110 to stop flow of power to the elements 120 and 122 if the voltage signals from the sensor 106 indicate that the output fluid temperature exceeds that maximum temperature. Although not shown in the Figures, the protector circuit 108, instead of the processor 111, may provide signals to system 112, in the event that the output fluid temperature exceeds the maximum temperature, to cause system 112 to indicate presence of a fault condition in the heater 10 and to provide an audible warning of same. The protection circuit 108 and switch 110 are connected to the circuit traces 144 and are disposed on substrate 142.

Processor 111 may also be adapted to detect when the power being supplied by supply 116 drops below a predetermined minimum threshold therefor necessary for proper operation of the heater 10, and to generate control signals for causing warning system 112 to indicate same by activating the "Lo Batt" LED and sounding an audible warning using the speaker comprised in system 112.

Preferably, the thickness of the portion of the member 65 defining the channel is about 0.032 inches, the width 58 of the channel 47 is 0.28 inches, and the thickness 60 of the fluid channel dividers of member 65 is about 0.060 inches. The total length of the heat exchanger 17 from the end 54 of the inlet 20 to the end 56 of the outlet 22 in this embodiment is about 3.71 inches and the length from one flared end (e.g., 16) to an opposite, flared end (e.g., 30) is about 2.25 inches. Each of the flexible walls 40, 42 is preferably 0.002 inches thick. Also preferably, each of the aluminum plates 136, 138 has a thickness of 0.040 inches and is 1.75 inches in length and width.

Figure 13:
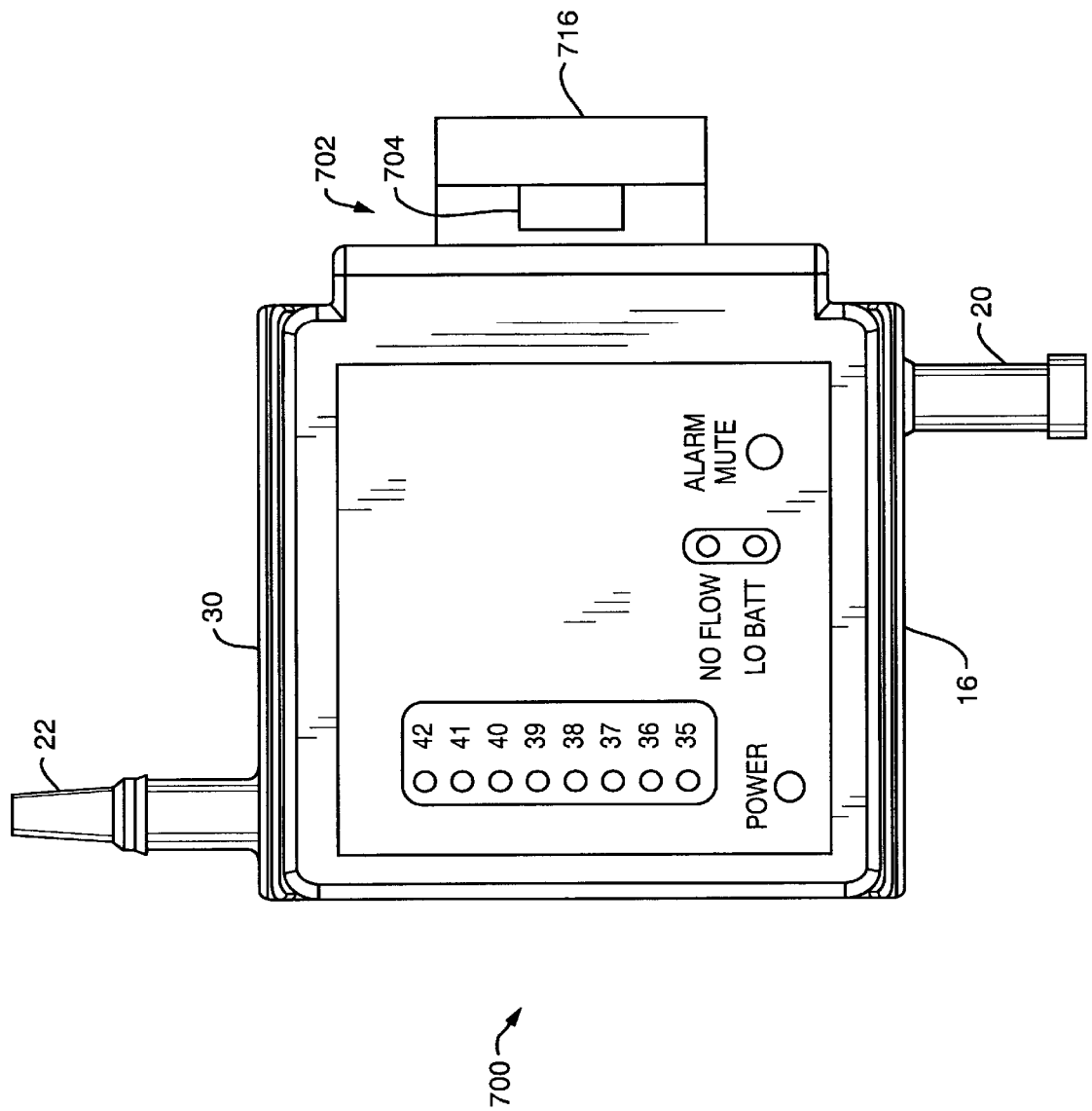
FIG. 13 is an outside perspective view of a variation of the embodiment of FIG. 1, which variation includes a controllable valve for stopping fluid flow through the heater if gas is present in and/or fluid flow through the heat exchanger is below a desired minimum therefor.
Figure 14:
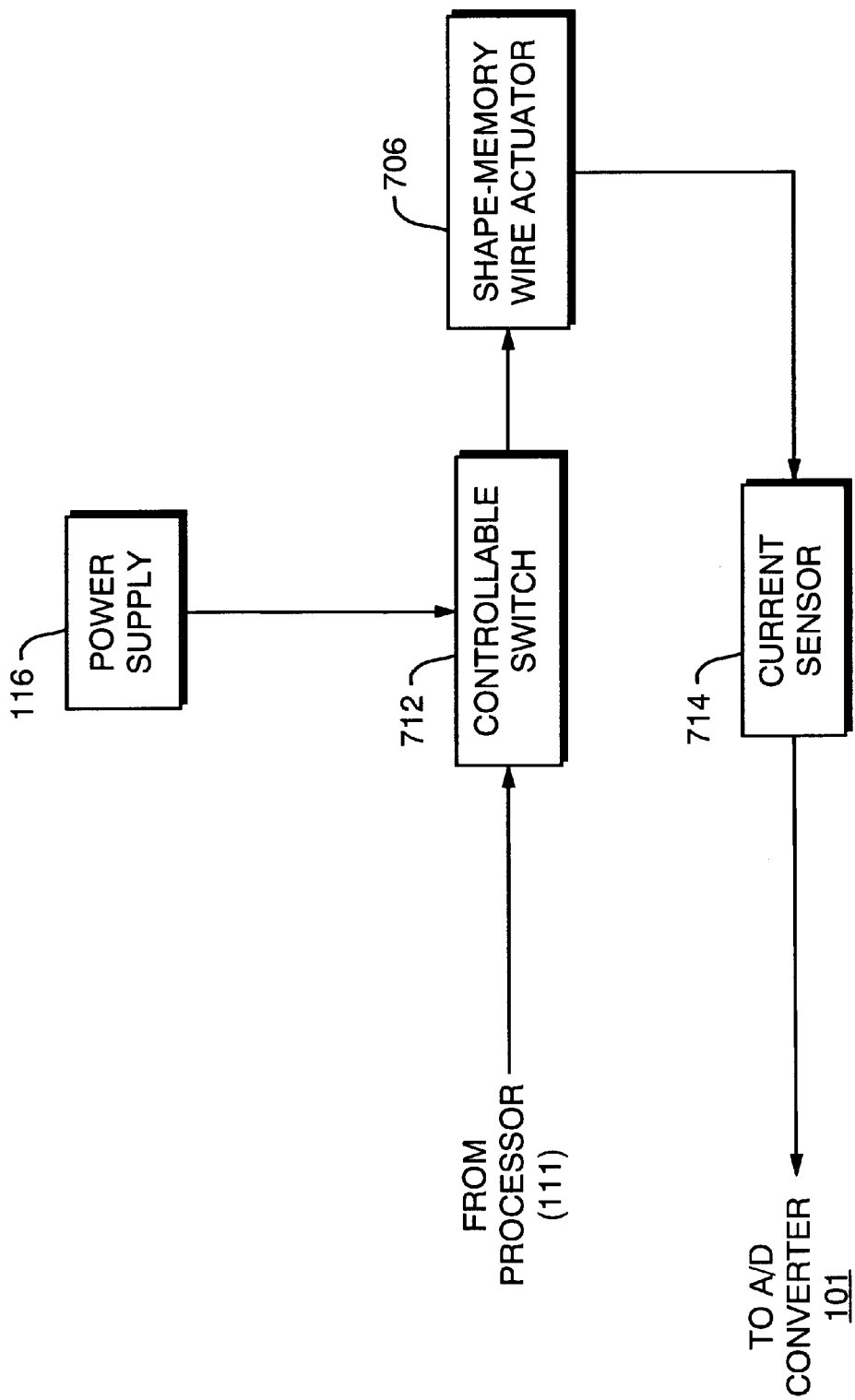
FIG. 14 is a highly schematic functional block diagram of electronics of the controllable valve system used in the variation of FIG. 13.
Figure 15:
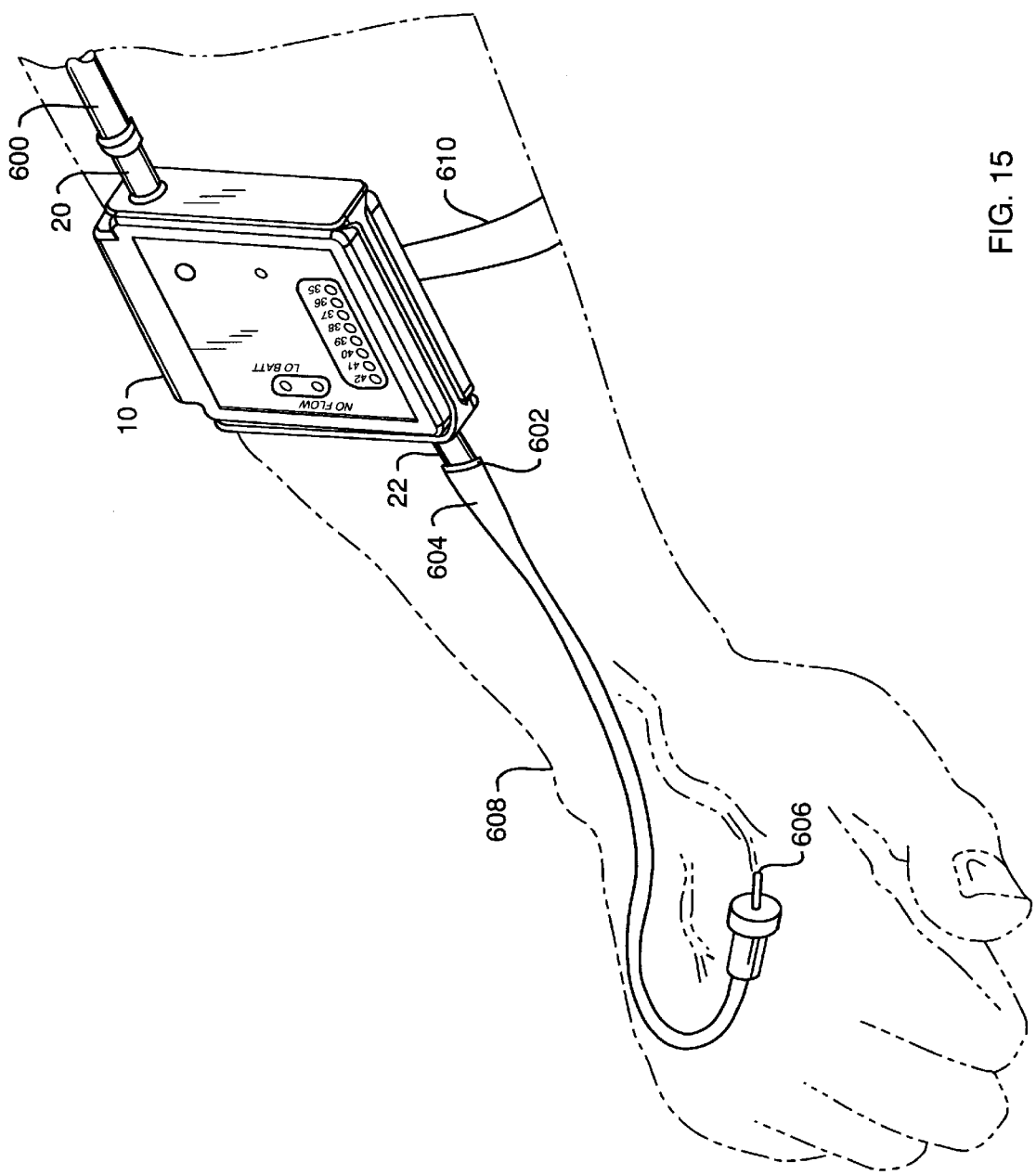
FIG. 15 shows the embodiment of FIG. 1 in use, being worn by a patient and delivering heated infusion fluid to the patient's infusion situs.
Figure 16:
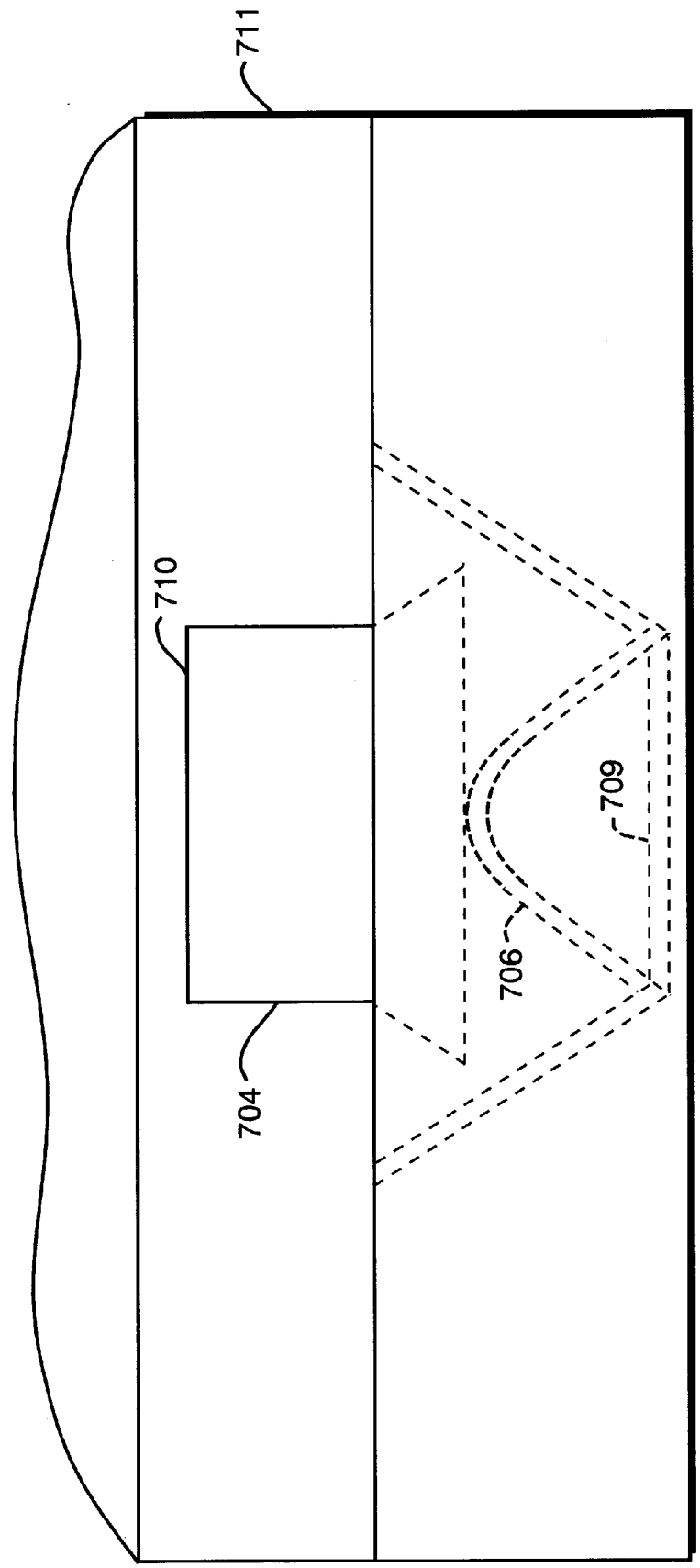
FIG. 16 is a schematic representation of the piston, tube choke channel, and memory wire actuator of the valve system of the variation of FIG. 13.

Turning now to FIGS. 13–14 and 16, a variation of the preferred embodiment of FIGS. 1–12 and 15 will now be described. In variation 700, the positions of various of the indicators are different from those in the embodiment of FIG. 1. Variation 700 also includes a valve system 702 comprising a piston member 704 (shown partially in ghost) that is actuated by a plastic spring 706 based upon changes in shape and/or length of a shape memory wire 709 (e.g., a nitinol-type wire) Both the spring 706 and wire 709 are shown in ghost in FIG. 16. The wire 709 changes shape and/or length when its temperature exceeds a transition temperature for such change, and returns to its original shape and/or length when its temperature passes below that transition temperature. More specifically, in this variation, the tubing connecting the output port 22 to the patient's infusion situs may be made to pass through a choke collar 711 attached to the housing 12. The wire 709 may be connected to the power source 116 via a controllable switch 712 whose state is controlled by control signals supplied thereto from processor 111. When power is supplied to the wire 709, the wire 709 heats up to transition temperature and changes shape so as to cause the spring 706 to impinge upon and push the piston 704. This causes a surface 710 of the piston to impinge upon and squeeze the tubing running through the choke collar sufficiently to cut off fluid flow through the tubing. A current sensor 714 may be connected to the wire (by conventional means, not shown) to sense the current flowing through the wire 709 and to provide the sensed current information to the processor 111 so as to enable the processor 111 to prevent overheating of the wire 709. After the power is cut off from the wire 709, the wire 709 cools to below its transition temperature and returns to its initial, relaxed shape and/or length (which in the variation of FIG. 16 is longer than that which is shown therein) that permits the fluidic pressure and natural elasticity of the tubing to force the piston out from the choke collar into housing portion 716 containing the spring 706 and wire 709. The processor 111 may be programmed to actuate the valve system in the event that the processor 111 detects presence of air or inadequate fluid flow rate in the path 43.

Thus, it is evident that there has been provided in accordance with the present invention a wearable infusion fluid heater that fully satisfies the aims and objects, and achieves the advantages, hereinbefore set forth. As will be appreciated by those skilled in the art, although the present invention has been described in connection with preferred embodiments and methods of use, many alternatives, modifications, and variations thereof are possible without departing from the present invention.

For example, although not shown in the Figures, each of the heating plates 136, 138 may include a plurality of grooves formed in the surfaces which contact the flexible walls 42, 40, respectively, directly above and below the fluid dividers in the heat exchanger 17. This increases the thermal resistances of the heat sinks 136, 138 in directions parallel to remaining planar portions of top and bottom surfaces, respectively, of the sinks 136, 138, and can increase the accuracy with which the processor 111 can control heating of the infusion fluid using the aforesaid techniques.

Other modifications are also possible. For example, rather than using the aforedescribed clamping valve mechanism for restricting fluid flow, the valve mechanism may instead comprise a pivoting lever (not shown) which is actuated by energization of a shape-memory wire attached to the lever to cut off fluid flow. Additionally, although the protection circuit 108 is shown in FIG. 7 as receiving the voltage signal output from the sensor 106, if heater 10 is appropriately modified, the circuit 108 may instead comprise its own thermistor-based temperature sensor.

In another modification, the processor 111 may be programmed to implement a diagnostic process upon being initially powered up, in which the processor 111 may cause the elements 120, 122 to maximally heat the fluid in the flow path 43 to a temperature above the predetermined maximum desired therefor, and thereafter, to determine whether the protection circuit 108 automatically deactivates the elements 120, 122 when the temperature at the outlet 92 exceeds that desired maximum. In this diagnostic mode, the processor 111 may be programmed also to determine if the length of time that it takes the heating elements 120, 122 to sufficiently heat the fluid in the flow path to cause the circuit 108 to deactivate the elements 120, 122 exceeds a maximum desired warm-up time.

Additionally, the processor 111 could alternatively be programmed to determine presence of inadequate flow rate through the flow path by determining whether the temperature difference between the input fluid temperature and the output fluid temperature does not fall within an empirically determined range expected for same, if the fluid flow rate were to exceed a desired level, at the power level supplied to the elements 120, 122.

Also, the processor 111 could be programmed to determine the actual flow rate in the flow path by determining the value of the "flow" variable as in the process of FIGS. 12A and 12B, and then using this value to determine therefrom the actual flow rate through the flow path based upon an empirical correlation programmed into the processor 111, which correlation is between experimentally measured flow rates through the flow path and respective values of the "flow" variable. The flow rate determined by the processor 111 to be present in the flow path may be indicated via LEDs (not shown) comprised in indicator/warming system 112, in a manner that is similar to that in which the fluid temperature is indicated via LEDs 51.

Accordingly, the present invention is intended to be viewed quite broadly as being limited only as set forth in the hereinafter appended claims.

What is claimed is:

1. A fluid heater, said heater comprising:
   a. a heat exchanger defining a flow path through said heater for fluid to be infused to a patient via a fluid infusion situs of said patient;
   b. at least one controllable heating element for heating the fluid in the flow path by heat conduction thereto through said heat exchanger; and
   c. a controller for controlling, based upon at least one temperature of the fluid in the flow path, heating of the fluid in the flow path by the heating element, said heating causing the fluid in the flow path to be substantially uniformly heated to a desired infusion temperature prior to exiting said heater, the at least one temperature of the fluid in the flow path being sensed by at least one temperature sensor that provides an indication of said at least one temperature to the controller;
   wherein the heat exchanger, the at least one heating element and the controller are all housed in a single housing dimensioned to be wearable by the patient adjacent the situs, and the controller also determines whether gas is present in the fluid based, at least partially, upon the at least one temperature.

2. A heater according to claim 1, wherein the controller is also for determining, based at least in part upon said at least one temperature, whether fluid flow rate in said flow path is below a desired threshold value therefor.

3. A heater according to claim 1, wherein said heating element comprises two heating elements, and said heat exchanger comprises two flexible walls for contacting respective heating elements.

4. A heater according to claim 3, wherein said heat exchanger also includes at least one member inserted between said flexible walls, which together with said flexible walls, defines the flow path.

5. A heater according to claim 4, wherein the flexible walls and member are made of plastic.

6. A heater according to claim 2, further comprising at least one indication system for being controlled by said controller and for providing a user-appreciable warning of when said flow rate is below said value.

7. A heater according to claim 1, further comprising an indicator for being controlled by said controller to provide a user-appreciable indication of when gas is present in said flow path.

8. A heater according to claim 1, wherein said heat exchanger is removable from said heater.

9. A heater according to claim 1, wherein said heating element comprises at least one metal plate for contacting said heat exchanger and an electrical resistance heater controlled by said controller for controllably heating said plate via heat conduction thereto.

10. A heater according to claim 1, wherein the controller is configured to determine an actual temperature of the fluid based upon the at least one temperature and a calculated temperature drop between the at least one heating element and the fluid in the flow path.

11. A heater according to claim 10, wherein the calculated temperature drop is determined by the controller based upon a heating energy being output by the at least one heating element and an empirically-determined thermal resistance between the at least one heating element and the fluid in the flow path.

12. A heater according to claim 1, wherein the heating of the fluid in the flow path is also based upon an empirically-determined relationship between a heating energy being supplied to the fluid in the flow path by the at least one heating element and an expected temperature increase in the at least one temperature of the fluid in the flow path.

13. A heater according to claim 1, wherein the controller determines whether the gas is present based upon whether an empirically-determined amount of time necessary to heat the fluid to the desired temperature if the fluid is not flowing is equal to an actual time required to heat the fluid to the desired temperature.

14. A heater according to claim 1, further comprising a valve for being automatically closed when gas is determined by said controller to be present in said flow path.

15. A heater according to claim 14, wherein said valve comprises an actuator made of shape-memory alloy.

16. A fluid heater, said heater comprising:
  a. a heat exchanger defining a flow path through said heater of fluid to be infused to a patient via a fluid infusion situs of said patient;
  b. at least one controllable heating element for uniformly heating the fluid in the flow path;
  c. a controller for controlling, based upon a temperature of the fluid in the flow path, heating of the fluid in the flow path by the heating element so as to cause the fluid in the flow path to be heated to a desired infusion temperature, the temperature of the fluid in the flow path being sensed by a temperature sensor that provides to the controller an indication of the temperature of the fluid in the flow path; and
  d. an attachment mechanism for releasably attaching a housing, containing the heating exchanger, the at least one heating element and the controller, to said patient adjacent to said fluid infusion situs;

wherein the controller also detects presence of gas in the fluid based, at least partially, upon the temperature.

17. A heater according to claim 16, further comprising at least one metal plate, a thermally conductive and electrically insulating layer, and an etched metal layer, said metal plate being for contacting both said heat exchanger and said insulating layer, and said etched metal is layer also for contacting said insulating layer.

18. A heater according to claim 17, wherein said controller and metal layer are comprised in a single circuit board laminated to said metal plate and insulating layer.

19. A heater according to claim 16, wherein said heat exchanger comprises two plastic flexible walls, said flexible walls each being bonded to a plastic member for defining, together with said flexible walls, said flow path.

20. A heater according to claim 16, wherein the controller is configured to determine an actual temperature of the fluid based upon the temperature and a calculated temperature drop between the at least one heating element and the fluid in the flow path.

21. A heater according to claim 20, wherein the calculated temperature drop is determined by the controller based upon a heating energy being output by the at least one heating element and an empirically-determined thermal resistance between the at least one heating element and the fluid in the flow path.

22. A heater according to claim 16, wherein the heating of the fluid in the flow path is also based upon an empirically-determined relationship between a heating energy being supplied to the fluid in the flow path by the at least one heating element and an expected temperature increase in the temperature of the fluid in the flow path.

23. A heater according to claim 16, wherein the controller determines whether the gas is present based upon whether an empirically-determined amount of time necessary to heat the fluid to the desired temperature if the fluid is not flowing is equal to an actual time required to heat the fluid to the desired temperature.

24. A fluid heater dimensioned so as to be wearable by a patient adjacent a fluid infusion situs of said patient, said heater comprising a completely solid heating element for heating to a desired temperature, by heat conduction, a fluid flowing in a flow path through said heater for infusion into said patient via said situs, the heater heating the fluid based upon at least one temperature of the fluid sensed by a temperature sensor, and a system for detecting presence of gas in the fluid based, at least partially, upon the at least one temperature of said fluid.

25. A heater according to claim 24, further comprising another completely solid heating element, each of said heating elements being positioned on respective opposite sides of said flow path.

26. A heater according to claim 24, wherein said heating element is also for substantially uniformly heating said fluid to said desired temperature.

27. A heater according to claim 24, wherein the system is configured to determine an actual temperature of the fluid based upon the at least one temperature and a calculated temperature drop between the at least one heating element and the fluid in the flow path.

28. A heater according to claim 27, wherein the calculated temperature drop is determined by the system based upon a heating energy being output by the at least one heating element and an empirically-determined thermal resistance between the at least one heating element and the fluid in the flow path.

29. A heater according to claim 24, wherein the heating of the fluid in the flow path is also based upon an empirically-determined relationship between a heating energy being supplied to the fluid in the flow path by the at least one heating element and an expected temperature increase in the at least one temperature of the fluid in the flow path.

30. A heater according to claim 24, wherein the system determines whether the gas is present based upon whether an empirically-determined amount of time necessary to heat the fluid to the desired temperature if the fluid is not flowing is equal to an actual time required to heat the fluid to the desired temperature.

31. A fluid heater comprising:
 a. a heating element for heating a fluid to be infused into a patient based upon a sensed temperature of the fluid; and
 b. a gas presence detection and warning system for detecting presence of gas in said fluid prior to infusion into said patient based, at least partially, upon the sensed temperature of said fluid and for providing a user-appreciable indication of when said gas is present in said fluid.

32. A heater according to claim 31, wherein said system comprises a processor for determining said presence based, at least partially, upon two different sensed temperatures of said fluid.

33. A heater according to claim 31, further comprising a valve controlled by said system for stopping flow of said fluid when said system detects the presence of said gas.

34. A heater according to claim 31, further comprising a removable protective enclosure for preventing contamination to said heating element and system.

35. A heater according to claim 31, wherein the system is configured to determine an actual temperature of the fluid based upon the sensed temperature and a calculated temperature drop between the heating element and the fluid.

36. A heater according to claim 35, wherein the calculated temperature drop is determined by the system based upon a heating energy being output by the heating element and an empirically-determined thermal resistance between the heating element and the fluid.

37. A heater according to claim 31, wherein the heating of the fluid is also based upon an empirically-determined relationship between a heating energy being supplied to the fluid by the heating element and an expected temperature increase in the sensed temperature.

38. A heater according to claim 31, wherein the system determines whether the gas is present based upon whether an empirically-determined amount of time necessary to heat the fluid to a desired temperature if the fluid is not flowing is equal to an actual time required to heat the fluid to the desired temperature.

39. An apparatus for heating fluid to be infused into a patient, comprising:
 a. a heating element for heating, based upon a sensed temperature of the fluid, a flow of said fluid prior to being infused into said patient; and
 b. a system for detecting when flow rate of said flow is below a minimum desired flow rate, for detecting presence of gas in the fluid based, at least partially, upon the sensed temperature of the fluid, and for providing a user-appreciation indication of when the flow rate of said flow is below said minimum desired flow rate and when the presence of gas is detected.

40. An apparatus according to claim 39, wherein said system comprises a processor for detecting when the flow rate of the flow is below said minimum flow rate based, at least partially upon, two different sensed temperatures of said fluid.

41. An apparatus according to claim 39, further comprising a valve controlled by said system for stopping said flow when said system detects that the flow rate of the flow is below said minimum flow rate.

42. An apparatus according to claim 39, wherein the system is configured to determine an actual temperature of the fluid based upon the sensed temperature and a calculated temperature drop between the heating element and the fluid.

43. An apparatus according to claim 42, wherein the calculated temperature drop is determined by the system based upon a heating energy being output by the heating element and an empirically-determined thermal resistance between the heating element and the fluid.

44. An apparatus according to claim 39, wherein the heating of the fluid is also based upon an empirically-determined relationship between a heating energy being supplied to the fluid by the heating element and an expected temperature increase in the sensed temperature of the fluid.

45. An apparatus according to claim 39, wherein the system determines whether the gas is present based upon whether an empirically-determined amount of time necessary to heat the fluid to a desired temperature if the fluid is not flowing is equal to an actual time required to heat the fluid to the desired temperature.

46. An apparatus for heating fluid to be infused into a patient, comprising:
 a. a heating element for heating a flow of said fluid prior to being infused into said patient based upon a sensed temperature of the fluid; and
 b. a system for detecting flow rate of said fluid, for detecting presence of gas in the fluid based at, least partially, upon the sensed temperature of the fluid, and for providing user-appreciable indication of said flow rate and said presence.

47. An apparatus according to claim 46, wherein the heating element and the system are both contained in a single housing dimensioned to be wearable by said patient adjacent to an infusion situs on said patient for said fluid.

48. An apparatus according to claim 46, wherein the system is configured to determine an actual temperature of the fluid based upon the sensed temperature and a calculated temperature drop between the heating element and the fluid.

49. An apparatus according to claim 48, wherein the calculated temperature drop is determined by the system based upon a heating energy being output by the heating element and an empirically-determined thermal resistance between the heating element and the fluid.

50. An apparatus according to claim 46, wherein the heating of the fluid is also based upon an empirically-determined relationship between a heating energy being supplied to the fluid by the heating element and an expected temperature increase in the sensed temperature.

51. An apparatus according to claim 46, wherein the system determines whether the gas is present based upon whether an empirically-determined amount of time necessary to heat the fluid to a desired temperature if the fluid is not flowing is equal to an actual time required to heat the fluid to the desired temperature.

* * * * *